United States Patent [19]

Nishigaki et al.

[11] Patent Number: 4,905,082
[45] Date of Patent: Feb. 27, 1990

[54] RIGID VIDEO ENDOSCOPE HAVING A DETACHABLE IMAGING UNIT

[75] Inventors: Shinichi Nishigaki, Tokyo; Takeaki Nakamura, Hino; Minoru Okabe, Musashino; Hitoshi Karasawa, Hachioji; Hiroyuki Kusnoki, Tokyo; Tadao Hagino, Yokohama; Tetsumaru Kubota, Hachioji; Mototsugu Ogawa, Hachioji; Masato Toda, Hachioji; Teruaki Sugata, Hachioji, all of Japan

[73] Assignee: Olympus Optical Co., Ltd., Tokyo, Japan

[21] Appl. No.: 190,724

[22] Filed: May 5, 1988

[30] Foreign Application Priority Data

| May 6, 1987 | [JP] | Japan | 62-110051 |
| May 6, 1987 | [JP] | Japan | 62-110059 |
| May 13, 1987 | [JP] | Japan | 62-116401 |
| May 13, 1987 | [JP] | Japan | 62-116406 |
| May 13, 1987 | [JP] | Japan | 62-117427 |
| May 15, 1987 | [JP] | Japan | 62-118663 |
| May 19, 1987 | [JP] | Japan | 62-121754 |
| May 20, 1987 | [JP] | Japan | 62-123356 |
| Oct. 27, 1987 | [JP] | Japan | 62-272609 |

[51] Int. Cl.⁴ .................... A61B 1/04; H04N 7/18
[52] U.S. Cl. ............................. 358/98; 128/6
[58] Field of Search .................... 358/98; 128/4-6; 350/573, 572, 413

[56] References Cited

U.S. PATENT DOCUMENTS

| 4,280,762 | 10/1988 | Nagasaki | 358/98 |
| 4,364,624 | 12/1982 | Lang et al. | 350/573 X |
| 4,440,157 | 4/1984 | Shishido | 128/6 |
| 4,491,865 | 1/1985 | Danna et al. | |
| 4,611,888 | 9/1988 | Prenovitz et al. | |
| 4,720,178 | 1/1988 | Nishioka et al. | 358/98 X |
| 4,779,613 | 10/1988 | Hashiguchi et al. | 128/6 |
| 4,786,965 | 11/1988 | Yabe | 358/98 |
| 4,799,104 | 1/1989 | Hosoya et al. | 358/98 |

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

An electronic endoscope system has an elongated rigid inserting section and a relay optical system disposed therein. The relay optical system transfers an optical image. A imaging device is disposed at a focus position of the relay optical sysetm in a face-to-face relationship with the imaging surface thereof.

35 Claims, 29 Drawing Sheets

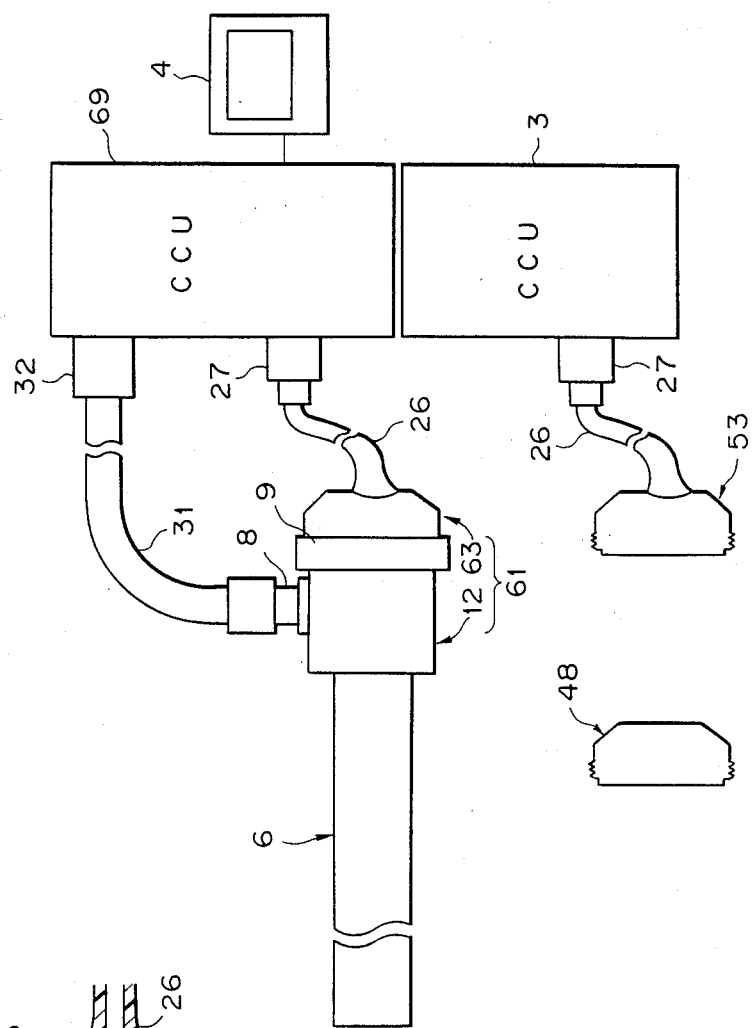
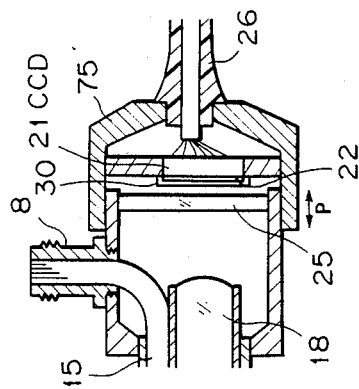
FIG. 9
FIG. 10

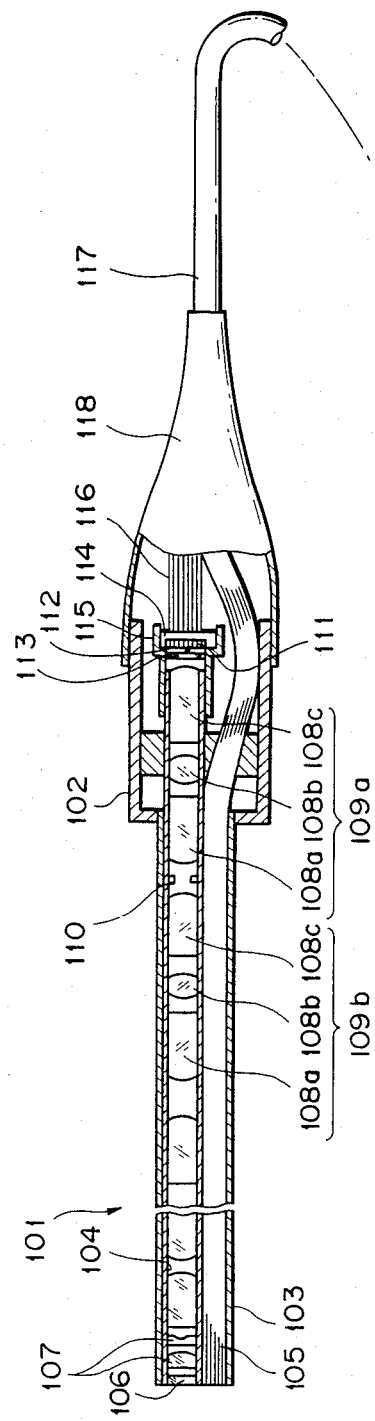
FIG.12
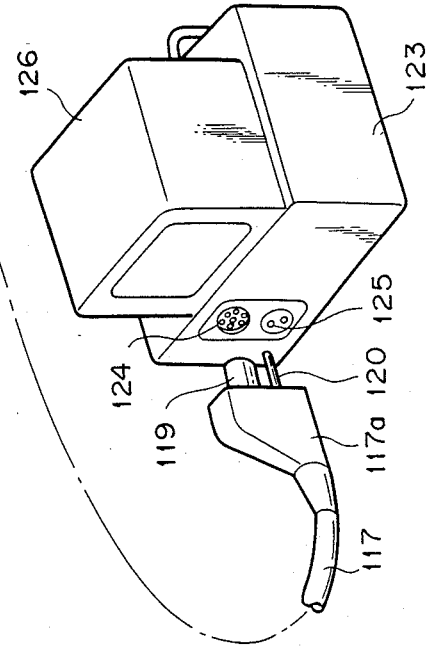
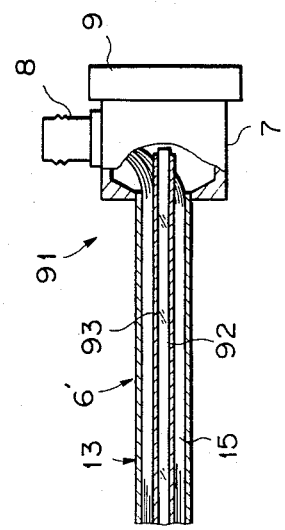
FIG.11

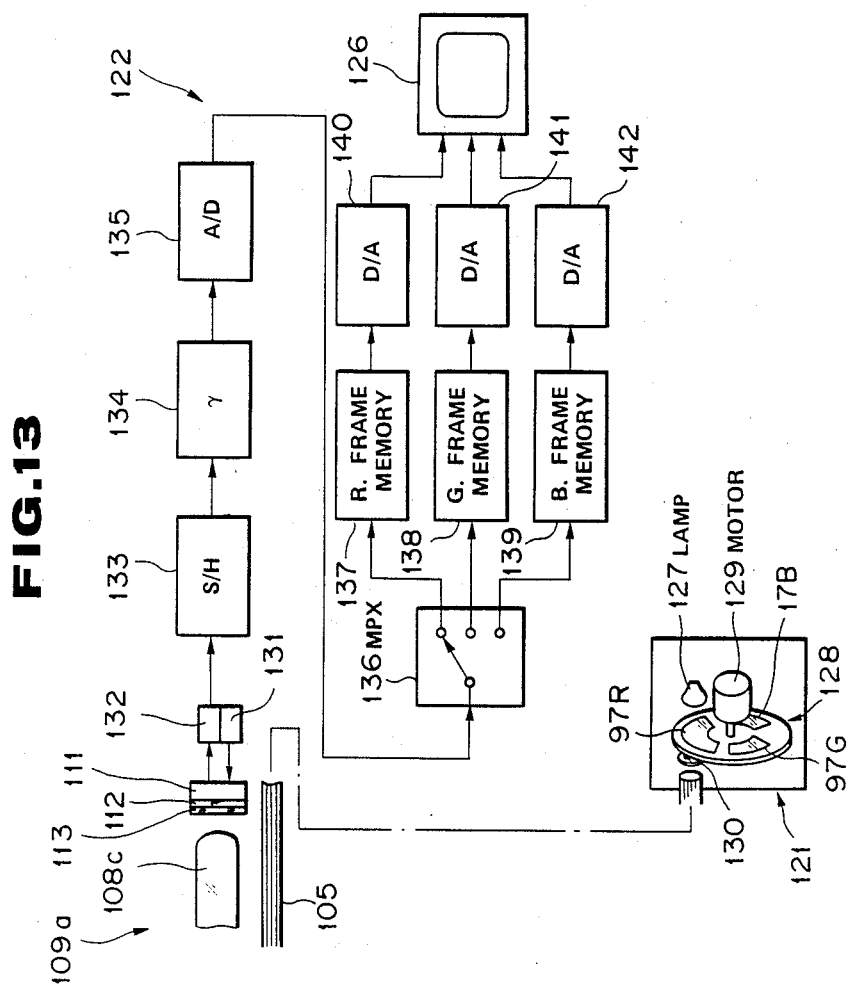

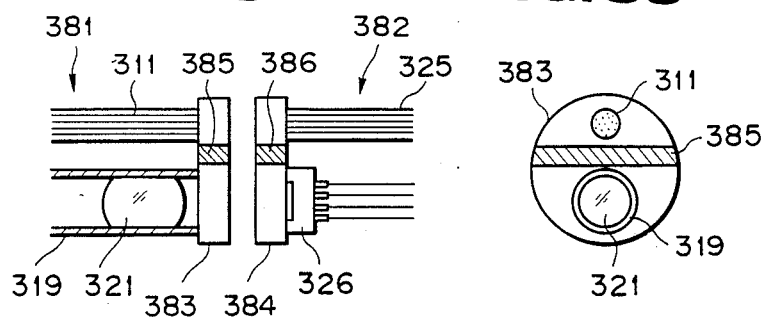
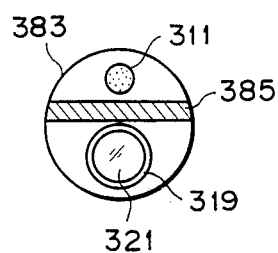
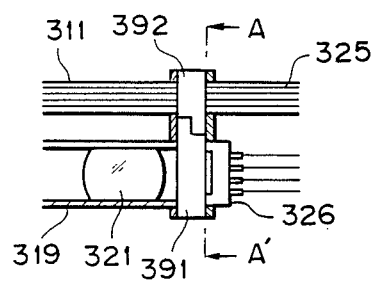
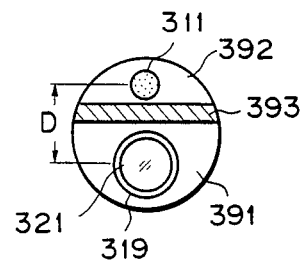
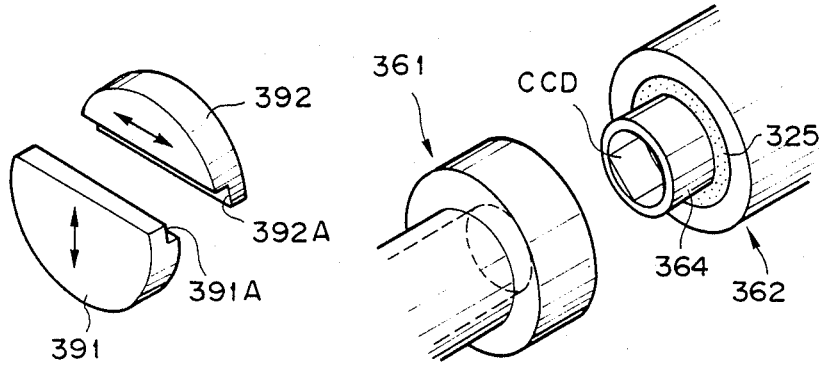

RIGID VIDEO ENDOSCOPE HAVING A DETACHABLE IMAGING UNIT

FIELD OF THE INVENTION AND RELATED ART STATEMENT

The present invention relates to a rigid video endoscope capable of focusing an optical image transferred through a relay optical system directly onto the imaging surface of a solid state imaging device without the need to pass the optical image through an eyepiece lens.

In recent years, various types of endoscope have been widely used. Such an endoscope typically has an elongated inserting section provided with an observing means at its distal end, and makes it possible to diagnose the affected part of the body without the need for discission, or to perform therapeutic treatments as required by using proper instruments.

The above-described endoscopes are classified into two major types: flexible endoscopes with flexible inserting sections and rigid endoscopes with rigid inserting sections.

The flexible endoscopes have the advantage that they can be inserted into bent hollow passages, while the rigid endoscopes can only be inserted into straight hollow passages. However, the rigid endoscopes are advantageous in that there is a high probability that they can spot a target portion. In addition, since the flexible endoscopes commonly require a flexible fiber bundle as an image guide for transferring an optical image rearwardly along the optical axis, their resolution is limited by the number of fibers which constitute the fiber bundle. However, since the endoscopes are capable of using a relay optical system as an image guide, they are advantageous in that the resolution can be enhanced as compared with the flexible endoscopes.

During a diagnosis using a rigid endoscope such as described above, there are some instances wherein a TV camera is attached to the eyepiece unit of the rigid endoscope to record an endoscopic image in preparation for subsequent detailed examinations or for the purpose of comparing variations in a symptom.

However, if the TV camera is attached to the eyepiece unit, this will lead to the problem that the weight of the rigid endoscope increases and hence the operation (e.g., insertion) thereof becomes difficult.

As a prior art example, an electronic scope is disclosed in, for example, U.S. Pat. No. 4,491,865. This electronic scope has an inserting section which accommodates a solid state imaging device at its distal end portion. However, in the electronic scope in which the solid state imaging device is accommodated in its distal end portion, this solid state imaging device occupies a greater part of the accommodation space therefor, and this makes it difficult to achieve a small diameter inserting section which can be realized, as in an endoscope using a relay optical system.

OBJECT AND SUMMARY OF THE INVENTION

It is, therefore, an object of the present invention to provide a rigid video endoscope which is light weight and is easy to operate.

It is another object of the present invention to provide a rigid video endoscope capable of producing a high resolution image.

It is still another object of the present invention to provide a rigid video endoscope capable of producing a clear image even in conditions in which the distance to an object greatly varies.

To achieve the above and other objects, in accordance with the present invention, there is provided a rigid video endoscope which is comprised of a focusing optical system provided in a rigid inserting section at the distal end portion thereof; a relay optical system having the function to receive at one end surface thereof an optical image focused by the focusing optical system, transfer the optical image toward the other end surface, and focus the optical image thereonto; and a solid state imaging device disposed at the focus position of the relay optical system, no eyepiece optical system being interposed between the solid state imaging device and the relay optical system. Accordingly, lightweight and good operability can be achieved.

BRIEF DESCRIPTION OF THE DRAWINGS

The invention will be better understood from the following description taken in conjunction with the accompanying drawings in which:

FIG. 9 is a sectional view of the essential portion of a fifth embodiment of the present invention;

FIG. 10 is a schematic illustration, with parts omitted for the sake of clarity, of a rigid video endoscope system according to a sixth embodiment of the present invention;

FIG. 11 is a partly sectional view illustrating in schematic form of a rigid video endoscope body according to a seventh embodiment of the present invention;

FIG. 12 is a diagrammatic illustration, in partial section, of an eighth embodiment of the present invention;

FIG. 13 is a circuit diagram illustrating the frame sequential video signal processing which is carried out in the eighth embodiment;

FIG. 34 is a partially sectional view of the essential portion of a twenty-first embodiment of the present invention;

FIG. 35 is a cross sectional view taken along the line X—X' of FIG. 34;

FIG. 36 is a partially sectional view of the essential portion of a twenty-second embodiment of the present invention;

FIG. 37 is a cross sectional view taken along the line A—A' of FIG. 36;

FIG. 38 is a perspective view of the polarizing plates used in the twenty-second embodiment;

FIG. 39 is a diagrammatic perspective view of the essential portion of a twenty-third embodiment of the present invention, with non-visible portions illustrated for better understanding;

DETAILED DESCRIPTION OF THE PREFERRED EMBODIMENTS

Preferred embodiments of the present invention will be described below with reference to the accompanying drawings.

Figure 2:
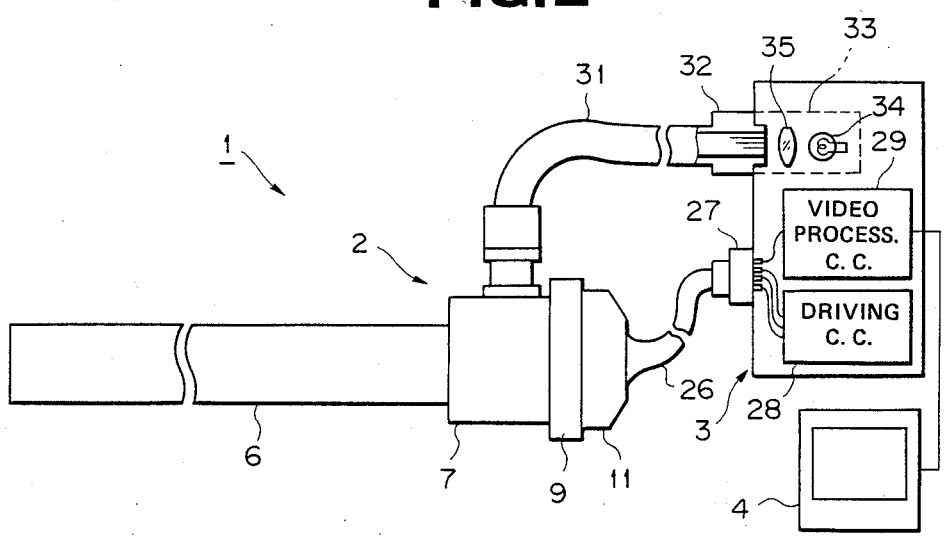
FIG. 2 is a schematic illustration, with parts omitted for the sake of clarity, of a rigid video endoscope system according to the first embodiment.

As schematically shown in FIG. 2, a rigid video endoscope system 1 according to a first embodiment comprises a rigid video endoscope 2 which can be inserted into a hollow organ to provide image signals relating to a portion to be observed; a camera control unit (hereinafter referred to as a "CCU") 3 to which the rigid video endoscope 2 according to the first embodiment is connected; and a color monitor 4 having a signal cable connected to a signal output terminal of the CCU 3 and providing a visual display of video signals which are input to the color monitor 4 through the signal cable.

The rigid video endoscope 2 is comprised of a rigid and elongated inserting section 6 and an operating section (grip section) 7 which is connected to the proximal end of the inserting section 6, and a light guide connector 8 is mounted to one side of the operating section 7. The operating section 7 is provided with a connection ring 9 for detachably connecting the operating section 7 to other equipment. If the connection ring 9 is rotated in a first direction, a rigid endoscope body 12 and an imaging unit 11 are connected with each other to form the integral rigid video endoscope 2 of the type shown in FIGS. 1 and 2. If the connection ring 9 is rotated in the reverse direction, the imaging unit 11 can be removed from the rigid video endoscope 2, and the rigid endoscope body 12 alone can be separated from the rigid video endoscope system 1 (see FIG. 4).

The inserting section 2 includes a tubular case 13 made from a steel metal such as a stainless steel, a lens tube 14, and a light guide 15 formed from an optical fiber bundle. The lens tube 14 and the light guide 15 are inserted in the the tubular case 13.

The distal end of the lens tube 14 is closed by a cover glass 16. An objective lens system 17 for focusing an image of an object is disposed in a portion of the lens tube 14 adjacent to the cover glass 16. Thus, the optical image focused by the objective lens system 17 is transferred rearwardly (to the right in FIG. 1) through a relay optical system 18 which is disposed within the lens tube 14 behind the objective lens system 17 along the optical axis thereof.

One end surface of the relay optical system 18, that serves as a light entrance face, is disposed in, opposing relationship with the focal plane of the objective lens system 17. An optical image, incident upon the light entrance face, is transferred to the other end surface, serving as a light exit face, through the intermediary of real images formed successively along the optical axis by a plurality of lenses which are serially arranged to form the relay optical system 18. The relay optical system 18 has another function of focusing the optical image transferred therethrough. A charge coupled device (hereinafter referred to as a "CCD") 21 is incorporated in the imaging section 11 which is fitted into and held by the connecting ring 9. The imaging surface of the CCD 21 faces the focal plane of the final relay lens element of the relay optical system 18. A color mosaic filter 22 constituted by a mosaic arrangement of primary color filters of red, green and blue is disposed on the optical axis ahead of the imaging surface of the CCD 21 so as to separate the optical image formed on that imaging surface into three color elements of red, green and blue.

The CCD 21 is fixed to a frame member 24 of the imaging unit 11 through a CCD fixing frame 23.

If the imaging unit 11 is removed from the operating section 7, a cover glass 25 appears which closes the side of the operating section on which the CCD 21 is disposed.

The structure of the above-described rigid video endoscope body 12 is designed so that it can withstand sterilization or disinfection in a sterilizing apparatus (for example, sterilization using steam at a pressure of 1 atm or higher and at a temperature of 120° C. or higher).

The CCD 21 is connected to one end of a signal cable 26, and the other end of the signal cable 26 is connected to a connector 27 so that a CCD drive signal can be applied from a driving circuit 28 to the CCD 21. In response to the application of the CCD drive signal, the CCD 21 outputs a read-out image signal to a video processing circuit 29. The read-out image signal is converted into a corresponding NTSC composite video signal by a video processing circuit 29, and a corresponding color visual display is provided at the color monitor 4.

It is to be noted that the front surface of the mosaic filter 22 of the imaging unit 11 which opposes the operating section 7 is covered by a transparent member 30 such as a cover glass. Therefore, the imaging unit 11 can be cleansed or disinfected using a disinfectant liquid.

Figure 3:
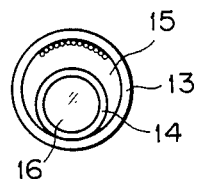
FIG. 3 is a cross sectional view illustrating a light guide which is inserted into the inserting section of the rigid video endoscope according to the first embodiment.

The light guide 15 is inserted into the axially extending space defined between the outer periphery of the lens tube 14 and the inner periphery of the tubular case 18 of the inserting section 6. The space has crescent-shaped cross section as shown in FIG. 3. A rear end portion of the light guide 15 is bent in the operating section 7 and is held in position by the light guide connector 8. As shown in FIG. 2, one end of a light guide cable 31 is connected to the light guide connector 8, and a light guide connector 32 provided at the other end of the light guide cable 31 is connected to a connector receiving portion of a light source section 33 incorporated in the CCU 3. Thus, white light emitted from a white light lamp 34 is converged and projected onto the light guide connector 32 by a condenser lens 35. The illumination light delivered to the light guide connector 32 is passed through the light guide 15 which extends through the light guide connector 32 and the inserting section 6, and is projected onto an object from the exit end of the light guide 15 that is exposed at the distal end surface of the inserting section 6. Thus, the object is illuminated by the illumination light emitted from that exit end surface.

Figure 5:
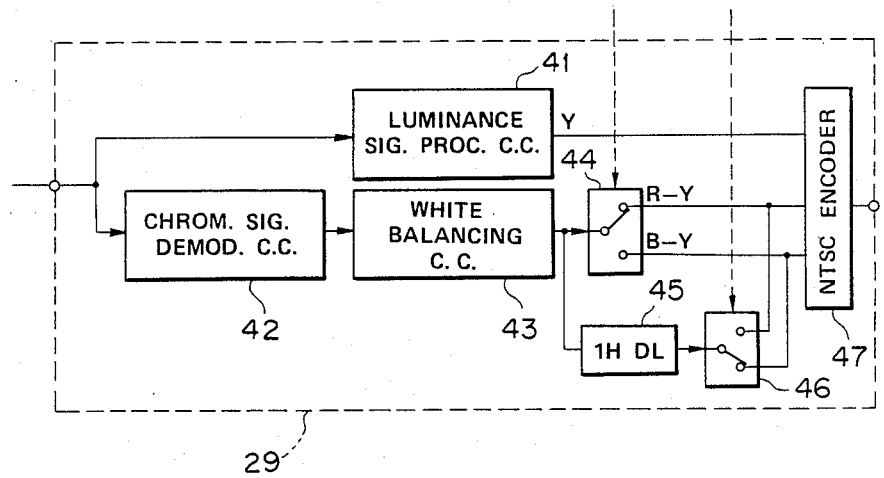
FIG. 5 is a circuit diagram illustrating the video processing circuit used in the first embodiment.

The previously-mentioned video processing circuit 29 has the construction shown in FIG. 5.

An output signal of the CCD 21 is fed to a luminance signal processing circuit 41 and a color signal demodulating circuit 42. The luminance signal processing circuit 41 generates a luminance signal Y from the input signal. The color signal demodulating circuit 42 generates color difference signals R-Y and B-Y for each horizontal line sequentially in time, and the color difference signals R-Y and B-Y are subjected to white balancing in a white balancing circuit 43. The signals in turn are applied directly to an analog switch 44 as well as an analog switch 46 after having been delayed by a one horizontal delay line 45 by a time interval equivalent to one horizontal line. Thus, the color difference singals R-Y and B-Y are provided in response to switching signals supplied from a timing generator (not shown).

Figure 4:
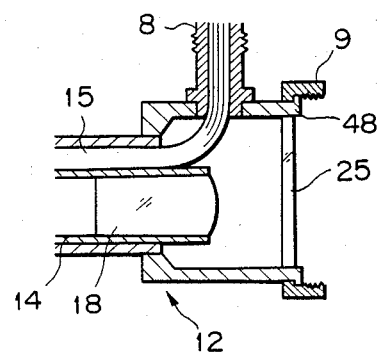
FIG. 4 is a fragmentary sectional view of the rigid video endoscope according to the first embodiment from which an imaging unit is removed.

As shown in FIG. 4, a recess 48 is formed in the rigid endoscope body 12 which serves as a positioning recess when the imaging unit 11 is to be attached to the rigid endoscope body 12, and the imaging unit 11 has a projection which is formed to fit the recess 48.

In the first embodiment having the above-described arrangement and construction, since no eyepiece unit is inserted between the CCD 21 and the relay optical system 18, the imaging surface of the CCD 21 directly faces the focal plane of the relay optical system 18 for transferring the optical image focused by the objective lens system 17. Therefore, the size and weight of the present endoscope can be reduced as compared with endoscope systems of a conventional type having an eyepiece portion to which a television camera is attached.

Accordingly, an operator can operate (e.g., insert) the present endoscope while supporting with one hand, weight substantially equal to (or lighter than) that of a rigid endoscope provided with no TV camera, without experiencing a lowering in operability due to the weight of the endoscope.

Furthermore, since the imaging unit 11 can be removed, the rigid endoscope body 12 which is inserted into a hollow organ can be fully sterilized or disinfected by a sterilizing apparatus such as an autoclave.

Therefore, even if the present endoscope is applied to a portion attacked by an infectious disease, it can be subjected to satisfactory sterilization, that is, it can be subjected to a sterilization process similar to that applied to ordinary rigid endoscopes. (As is known, flexible endoscopes are generally inferior to rigid endoscopes in respect of resistance to sterilization). The mosaic filter 22 is low in resistance to temperatures but, in the first embodiment, is incorporated in the imaging unit 11 detachably attached to the operating section 7 which is not inserted into a hollow organ. Therefore, a sufficient sanitary effect can be achieved only by disinfection using a disinfectant liquid.

Figure 6:
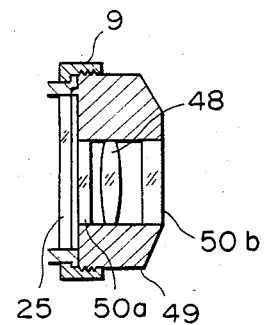
FIG. 6 is a diagrammatic sectional view of an eyepiece unit according to a second embodiment of the present invention.

FIG. 6 shows an eyepiece unit according to a second preferred embodiment of the present invention. The second embodiment is a modified version of the first embodiment in which, when the imaging unit 11 is removed from the operating section 7 as shown in FIG. 4, an eyepiece unit 49 which accommodates an eyepiece lens 48 can be attached as required to the operating section 7 for visual observation.

A through hole in which the eyepiece lens 48 is mounted is covered at its opposite ends by cover glasses 50a and 50b, respectively, to prevent dust from adhering to the lens 48.

In this case, this eyepiece unit 49 can be reduced in size without the need to form its configuration into the shape which provides for attachment of a TV camera. (In order to facilitate attachment of a TV camera, many of conventional eyepiece units have eyepiece window portions whose external configuration is formed into a conical shape which progressively increases in diameter axially in the rearward direction.)

In accordance with the second embodiment, an endoscopy can be performed by a combination of the light source section 33 and the eyepiece unit 49 without using the CCU 3 or color monitor 4 such as are shown in FIG. 2.

Figure 7:
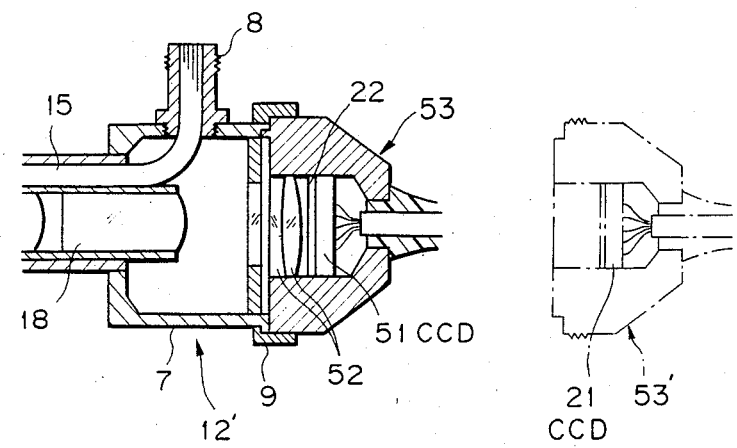
FIG. 7 is a sectional view of the essential portion of a third embodiment of the present invention.

FIG. 7 shows the essential portion of a third preferred embodiment of the present invention.

In the third preferred embodiment, a magnifying unit 53 is constituted by a CCD 51 which includes more picture elements than the CCD 21 of the first embodiment and a magnifying lens system 52 which is disposed ahead of the CCD 51 on the optical axis thereof.

In the third embodiment, the incorporation of the magnifying lens system 52 enables use of the CCD 51 having still more picture elements. It is, therefore, possible to select a desired image resolution in accordance with the resolution realized by the objective lens system 17 and the relay optical system 18. As shown by one-dot chain lines in FIG. 7, an imaging unit 53' provided with the CCD 21 having no magnifying lens system 52 may be attached to the third preferred embodiment.

In this embodiment, the frame of the operating section 7 of a rigid endoscope body 12' has an annular shape which is concentric with the optical axis of the relay optical system 18. The magnifying lens system 52 and the CCD 51 of the imaging unit 53 as well as the CCD 21 of the imaging unit 53' are designed so that, after assembly, each of their optical axes corresponds to the optical axis of the relay optical system 18.

The third embodiment employs the CCD 51 whose resolution is equal to or higher than the resolution realized by the objective lens system 17 and the relay optical system 18. It is accordingly possible to sufficiently enhance the resolution of a picture image displayed on the color monitor 4. Furthermore, the influence of a signal processing system which might cause a deterioration in resolution can be reduced.

Figure 8:
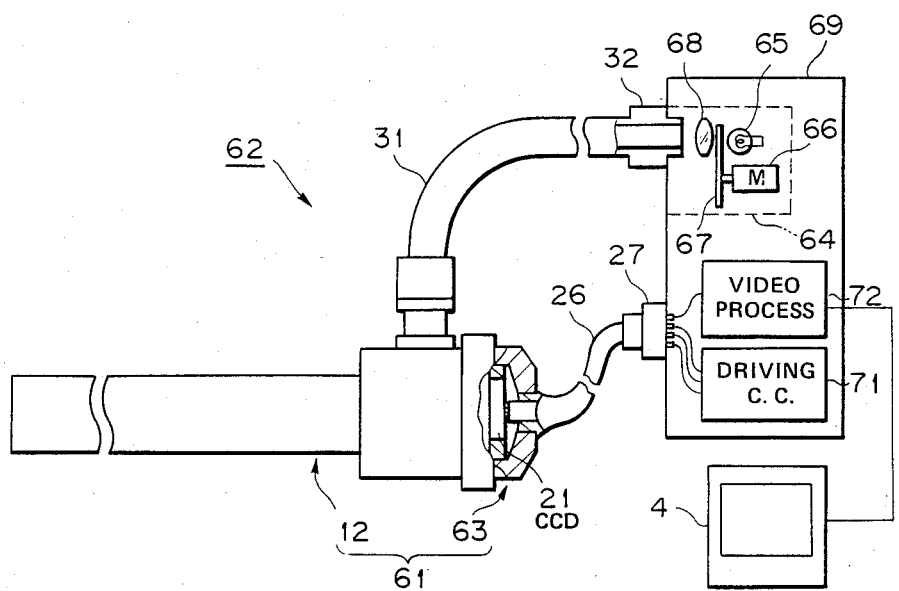
FIG. 8 is a schematic illustration, with parts broken away and other parts omitted for the sake of clarity, of a rigid video endoscope system which includes a rigid video endoscope according to a fourth embodiment of the present invention.

FIG. 8 schematically shows a rigid video endoscope system 62 equipped with a rigid video endoscope 61 according to a fourth preferred embodiment of the present invention.

Figure 1:
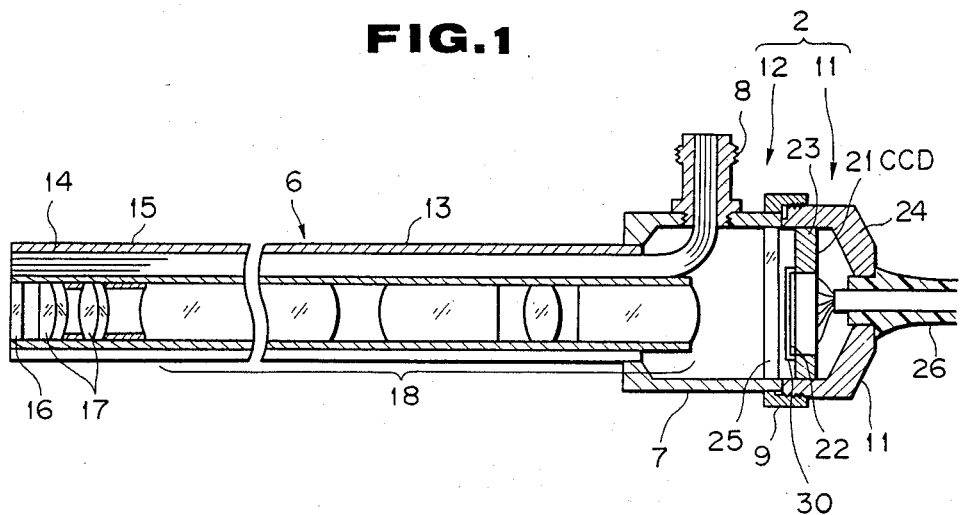
FIG. 1 is a diagrammatic illustration, with parts in section and other parts omitted for the sake of clarity, of a rigid video endoscope according to a first embodiment of the present invention.

The rigid video endoscope system 2 shown in FIG. 1 differs from the rigid video endoscope system 62 in that an imaging unit 63 including the CCD 21 having no mosaic filter 22 is employed, but the rigid endoscope bodies 12 of the above-described embodiments and the fourth embodiment have the same construction.

In the fourth embodiment, the connector 32 of the light guide cable 31 is connected to a frame sequential type of light source section 64. White light from a white light lamp 65 is passed through a rotating filter 67 which is driven by a motor 66, and is separated into individual wavelengths corresponding to red, green and blue. Thus, light having each of the wavelengths is supplied through a condenser lens 68 to the connector 32. An object is illuminated by the light having each of the wavelengths, and an image of the object is formed on the CCD 21. In response to the application of a CCD drive signal from a driving circuit 71 of a CCU 69, an image signal is read from the CCD 21.

The output signal from the CCD 21 is supplied through the signal cable 26 to a frame sequential type video processing circuit 72 incorporated in the CCU 69, converted into, e.g., a corresponding NTSC composite video signal by the circuit 72, and displayed in color at the color monitor 4. If a CCD having the same number of picture elements is employed, the above-described frame sequential system can achieve resolution which is approximately three times that of a simultaneous system which produces a color image by means of illumination with white light.

FIG. 9 shows the essential portion of a fifth preferred embodiment of the present invention.

The fifth embodiment is a modified version of the first embodiment shown in, for example, FIG. 1 in that the imaging unit 11 has a frame member 75 which enables the imaging unit 11 to slide with respect to the operating section 7 along the optical axis in the directions indicated by an arrow P. This arrangement constitutes a focus adjustment means which enables a focusing operation by moving the CCD 21 forwardly and backwardly along the optical axis.

The focus position of the optical system varies depending upon variations in the distance to an object, but in accordance with the fifth embodiment, the imaging surface of the CCD 21 is always held in proper focus position. Therefore, even if the object distance varies, a clear picture image which is in focus can be displayed on the color monitor 4.

In general, fixed focus arrangements are adopted in electronic scopes of the type in which a CCD is fixed at the focus position of an objective lens system. For this reason, if the object distance greatly varies, the optical system is defocused, so that a clear image cannot be provided. Similar shortcomings are involved with flexible endoscopes of the type which includes an image guide constituted by a fiber bundle.

On the other hand, in the present endoscope using the relay optical system 18 which transfers an optical image in such a way that a succession of real images are formed, the focus position on which an optical image is formed by the optical transfer varies if the object distance changes. In this embodiment, the position of the imaging surface of the CCD 21 can be adjusted in accordance with the variations in the focus position. Accordingly, even when an endoscope according to the fifth embodiment is used under situations in which an object distance varies over a wide range, a sharp display of an image can be provided and thus an operator can make a proper diagnosis.

FIG. 10 schematically shows a rigid video endoscope system 81 according to a sixth preferred embodiment of the present invention.

The rigid video endoscope system 81 comprises the rigid video endoscope system 62, as illustrated in, for example, FIG. 8, including the rigid video endoscope 61 of a frame sequential system, the frame sequential type CCU 69 associated with the endoscope 61, and the color monitor 4; the built-in color filter type imaging unit 53; the CCU 3 associated with the imaging unit 53; and the eyepiece unit 48.

The rigid video endoscope system 81 is adapted for use as an ordinary rigid endoscope by attaching the eyepiece unit 48 to the rigid endoscope body 12. In this case, the connector 32 is connected to the CCU 3 and white light from the CCU 3 is used as illumination light.

In addition, the rigid video endoscope system 81 can be used as a rigid video endoscope apparatus whichever of the imaging units 63 and 53 is attached to the rigid video scope body 12.

An one example, if a portion which shows movement needs to be observed, the built-in color filter type imaging unit 63 can be used to produce an image free of a substantial blur. As another example, if a portion which shows no large movement but requires high resolution needs to be observed, the imaging unit 53 can be used to provide a high resolution image. (In these examples, it is assumed that the two imaging units 63 and 53 have the same number of picture elements.)

This rigid video endoscope system 81 can be adapted for different applications by selecting a proper one of the imaging units 63 and 53.

FIG. 11 shows the essential portion of a rigid video endoscope body 91 according to a seventh preferred embodiment of the present invention.

The rigid video endoscope body 91 differs from the rigid endoscope body 12 shown in, for example, FIG. 1 in that the objective lens system 17 and the relay optical system 18 are constituted by a single gradient index lens 92 such as a so-called SELFOC lens. The lens 92 has a columnar shape and a refractive index which is distributed along its optical axis. Basically, the lens 92 has a function equivalent to that realized by a serial arrangement of convex lenses.

The diameter of the lens 92 can be made smaller than that of the previously-described relay optical system constituted by a plurality of convex lenses which are arranged in series at predetermined intervals, so that an extremely thin inserting section 6' can be obtained. This enables the inserting section 6' to be inserted into a remarkably narrow hollow organ.

By way of example, in the endoscope body 91, a lens tube 93 accommodating the lens 92 extends along the axis of the inserting section 6'. However, as in the endoscope body 12 shown in FIG. 1, the lens tube 93 may be disposed eccentrically with the axis of the inserting section 6'. As a matter of course, the imaging unit 53' or the like shown in FIG. 7 may be attached to the endoscope body 91.

Although FIG. 11 shows an example in which the lens 92 has the functions of both a relay optical system and an objective lens system, the lens 92 may be provided with the function of only the relay optical system.

In addition, the respective embodiments described above may be combined to construct various modified forms.

FIG. 12 shows an eighth preferred embodiment of the present invention.

As illustrated, a rigid video endoscope indicated generally at 101 is comprised of an operating section 102 which also serves as a grip which is hand held by an operator. A rigid inserting section 103 extends forwardly from the operating section 102 and has a straight elongated form. A lens tube 104 and a light guide 105 constituted by a fiber bundle extend from the operating section 102 into the inserting section 103 in parallel with each other along the axis of the inserting section 103. The distal end of the light guide 105 forms a light exit end at the distal end surface of the inserting section 103. On the other hand, the lens tube 104 extends to the distal end of the inserting section 103, and includes a cover glass 106 at its distal end and an objective lens system 107 behind of the cover glass 106 along the optical axis. Further, a plurality of relay lens groups 109a, 109b, . . . , each having a plurality of relay lens elements 108a, 108b and 108c are arranged in series in the portion of the lens tube 104 between the rear of the objective lens system 107 and the operating section 102. A visual field mask 110 is disposed in the focus position ahead of the final-stage relay lens group 109a while a solid state imaging device 111 is disposed in the focus position behind the same relay lens group 109a. The visual field mask 110 may be disposed in one of the focus positions ahead of the relay lens groups 109b, ..., other than the final-stage relay lens group 109a.

The solid state imaging device 111 is stationarily connected to a board 114 by a bonding wire (not shown) with a protection filter 112 and an infrared cutoff filter 113 bonded to its front surface, and the board 114 is mounted to the proximal end of the lens tube 104 by means of a frame 115. A multiplicity of signal lines 116 are connected to the board 114.

One end of a flexible cable 117 is, for example, integrally connected to the rear end of the operating section 102 through a connecting section 118, and the light guide 105 and the signal line 116 extend into the cable 117. The cable 117 has a connector 117a at its other end, and the connector 117a is provided with a plug 119 for the electrical line and a plug 120 for the optical line.

A control apparatus 123 which includes a light source device 121 and a video signal processing circuit 122 both of which will be described later has a socket 124 for the electrical line and a socket 125 for the optical line so as to receive the plugs 119 and 120 of the connector 117a, respectively. A color CRT 126 serving as a display means is connected to the control apparatus 123.

As shown in FIG. 13, the light source device 121 incorporated in the control apparatus 123 is provided with a light source lamp 127 and a rotary color filter 128 constituted by three primary color filters 97R, 97G and 97B which transmit red, green and blue, respectively, and a rotary wheel 98 in which these three color filters are mounted. The rotary color filter 128 is rotated by, for example, a stepping motor 129. Illumination light from the light source lamp 127 is sequentially separated into wavelengths of red, green and blue, converged by a condenser lens 130, passed through the light guide 105 in the cable 117, and emitted from the exit end of the inserting section 103. Thus, a portion to be observed is illuminated by the illumination light in a frame sequential manner.

Reflected light of each color light of red, green and blue from the portion to be observed is transmitted through the objective lens system and the relay lens system, and is received by the image area of an imaging chip buried in the solid state imaging device 111. In a frame sequential system, output signals from the image area of the imaging chip are subjected to a video signal processing as shown in, for example, FIG. 13.

More specifically, signals corresponding to the picture elements of the solid state imaging device 111 are output, for example, sequentially and horizontally, in response to clock signals applied from a driving circuit 131. The thus-obtained electrical signals containing image information are amplified by a preamplifier 132 and video signals are extracted from the electrical signals by a sample and hold circuit 133. The video signals are subjected to gamma correction in a gamma correction circuit 134, then converted into digital signals by an A/D converter 135. These electrical signals are switched by a multiplexer 136 in synchronism with frame sequential illumination, and are sequentially stored in an R frame memory 137, a G frame memory 138, and a B frame memory 139 which correspond to red, green and blue, respectively. The video signals are read from the respective frame memories 137, 138 and 139, simultaneously and horizontally, at a speed which matches a display device such as the color CRT monitor 126. The signals thus read are converted into analog signals by corresponding D/A converters 140, 141 and 142 to provide R, G and B color signals. These R, G and B color signals are input to the color CRT monitor 126 so that the portion desired to be observed is displayed in color.

In this arrangement, the visual field mask 110 which is disposed at the focus position ahead of the relay lens group 109a blocks dim marginal light or light diffusely reflected from the marginal portion or the like of the relay lens group, and only a clear endoscopic image is made incident upon the solid state imaging device 111.

Figure 14:
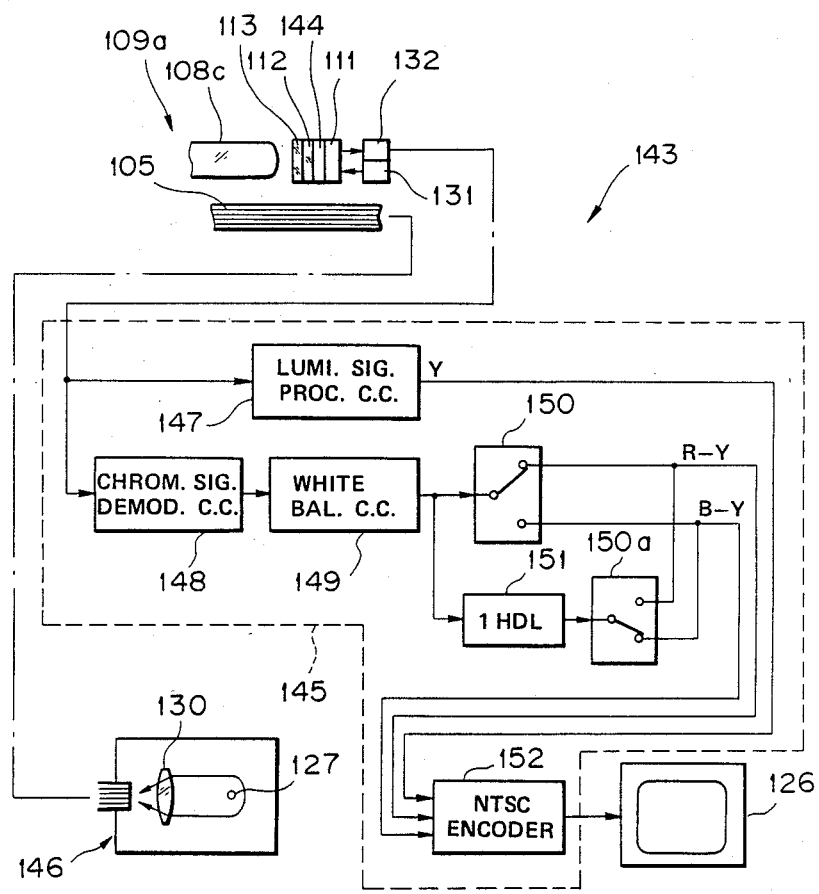
FIG. 14 is a diagrammatic illustration of the control unit and associated circuitry of a rigid electronic endoscope according to a modified form of the eighth embodiment which adopts a built-in color filter system.

FIG. 14 is a diagrammatic illustration of the control unit and associated circuitry of a rigid video endoscope according to a modified form of the eighth preferred embodiment of the present invention which adopts a built-in color filter system.

In this modified form, a color mosaic optical filter 144 is disposed between the protection filter 112 and the solid state imaging device 111 disposed at the focus position ahead of the final-stage relay lens group 109a.

The control apparatus 123 is provided with a mosaic type processing circuit 145 as shown in FIG. 14 and a light source device 146. The light source device 146 is essentially constituted by the light source lamp 127 and the condenser lamp 130. White light radiated from the light source lamp 127 is converged by the condenser lens 130 and is made to enter the light guide 105 constituted by the fiber bundle within the aforesaid cable 117. Thus, the light is projected from the distal end of the inserting section 103 onto a portion desired to be observed.

White light reflected from the portion to be observed is transmitted through the objective lens system and the relay lens system, passed through the protection filter 113 and the infrared cutoff filter 112 disposed ahead of the solid state imaging device 111, and conducted into he color mosaic optical filter 144. Thus, the white light is separated into primary color elements of red, green and blue by the color mosaic optical filter 144.

Light containing each of the color elements of red, green and blue is received by the image guide area of the imaging chip. In a simultaneous system, electrical signals containing image information from the imaging chip are subjected to a video signal processing as shown in, for example, FIG. 14.

More specifically, signals corresponding to respective picture elements of the image area of the imaging chip are output, for example, horizontally and sequentially, in synchronism with driving signals output from the driving circuit 131. The electrical signals are amplified by the preamplifier 132, and input to the luminance signal processing circuit 147 and the color signal demodulating circuit 148. Thus, the luminance signal processing circuit 147 generates a luminance signal Y. The color signal demodulating circuit 148 generates color difference singals R-Y and B-Y for each horizontal line sequentially in time, and the color difference signals R-Y and B-Y are subjected to white balancing in the white balancing circuit 149. The signals are applied directly to an analog switch 150 as well as an analog switch 150a after having been delayed by a one horizontal delay line 151 by a time interval equivalent to one horizontal line. Thus, the color difference signals R-Y and B-Y are generated in response to switching signals supplied from a timing generator (not shown). The luminance signal Y and the color difference signals R-Y and B-Y are multiplexed by an NTSC encoder 152, and are input to the color CRT monitor 126 at which the portion desired to be observed can be displayed in color.

Figure 15:
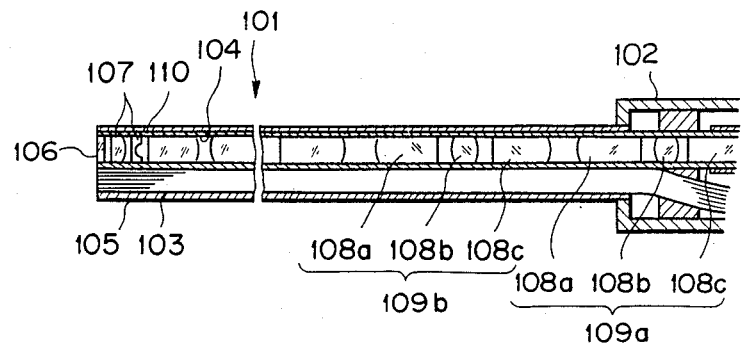
FIG. 15 is a partially sectional view of the essential portion of a rigid electronic endoscope according to a ninth embodiment of the present invention.

FIG. 15 is a cross sectional view of the essential portion of the rigid video endoscope according to a ninth preferred embodiment of the present invention.

This embodiment is a modified version of the eighth embodiment in that the visual field mask 110 is disposed in the focus position of the objective lens system 107 in the vicinity of the distal end of the inserting section 103.

Figure 16:
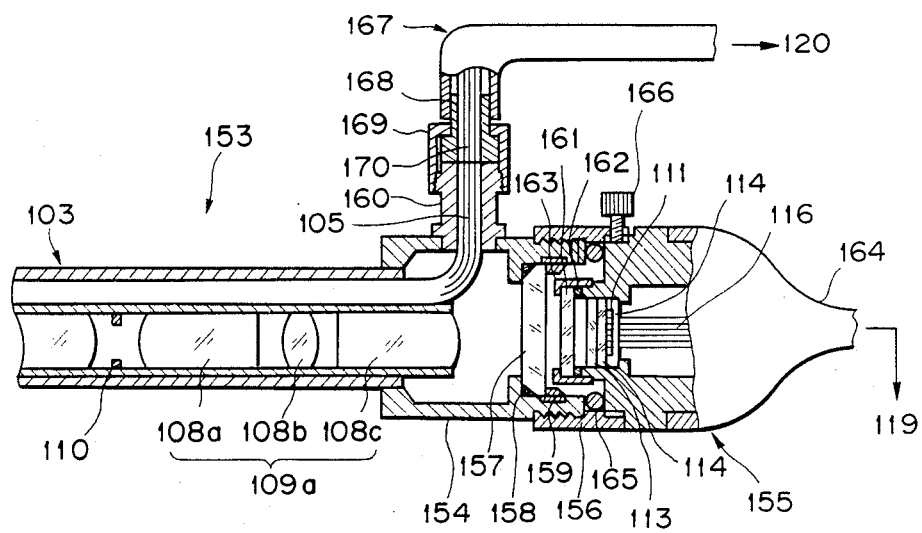
FIG. 16 is a partially sectional view of the essential portion of the control unit and associated circuitry of a rigid electronic endoscope according to a tenth embodiment which adopts a built-in color filter system.

FIG. 16 is an illustration, with essential portions cut away, of the operating section and associated portions of a rigid video endoscope according to a tenth embodiment of the present invention.

In the tenth embodiment, an externally threaded portion is partially formed around the outer periphery of an operating section 154 and an internally threaded portion is partially formed around the inner periphery of a connecting ring 156 which is rotatably fitted onto the outer periphery of an imaging section 155. The internally threaded portion is screwed into the externally threaded portion so that the operating section 154 is detachably connected to the imaging section 155 which stationarily holds the board 114 containing the solid state imaging device 111 to which the infrared cutoff filter 113 and the protection filter 112 are bonded. A cover glass 157 is fitted into the rear end aperture of the operating section 154 and is tightly pressed against the inner periphery of the aperture through an O ring 158 by the fastening forces of fixing screws 159. A light guide connector 160 is provided on a side portion of the operating section 150 to fix the light guide 105 so that the rigid video endoscope 153 including the operating section 154 is endowed with a watertight structure. A cover glass 161 is tightly pressed against the imaging section 155 via an O ring 162 by the fastening forces of fixing screws 163, ahead of the infrared cutoff filter 113. A cable 164 which includes the signal lines 116 extending from the board 114 is connected to the rear end of the imaging section 155 so that the imaging section 155 is also provided with a watertight structure. An O ring 165 is disposed between the opposing end surfaces of the operating section 154 and the imaging section 155 so that when the sections 154 and 155 are connected to each other, the O ring 165 is held in compression therebetween. The O ring 165 functions to prevent water from flowing into the space between the opposing external surfaces of the cover glasses 157 and 161 and to adjust the distance therebetween so that the solid state imaging device 111 may be disposed at the focus position of light rays transmitted through the final-stage relay lens element 108c and passed through the cover glasses 157 and 161, the infrared cutoff filter 113, and the protection filter 112. A screw 166 is screwed into a through hole in the connecting ring 156 radially inwardly from its outer periphery and the inner end of the screw 166 is brought into contact with the outer periphery of the imaging section 155. If the screw 166 is further tightened, the connecting ring 156 can be fixed with respect to the imaging section 155.

An externally threaded portion is formed around a portion of the outer periphery of the light guide connector 160, and an internally threaded portion is formed around a portion of the inner periphery of a connecting ring 169 which is rotatably fitted onto a connector 168 of the light guide cable 167. When the internally threaded portion is screwed into the externally threaded portion, the light guide 105 is detachably connected to a light guide 170 in the light guide cable 167 in end-to-end relationship. The extending end of the cable 164 is provided with the electrical-line plug 119 and the extending end of the the light guide cable 167 is provided with the optical-line plug 120, and the plugs 119 and 120 are connected respectively to the electrical-line sockets 124 and 125 of the control apparatus 123. Thus, the portion desired to be observed is displayed in color by the control apparatus 123 of a frame sequential system. As a matter of course, the color mosaic optical filter 144 described previously may be incorporated to constitute a built-in color filter system.

In the above-described arrangement, the image of the visual field mask is formed on the imaging surface of the solid state imaging device to cover the marginal portion of an endoscopic image. Therefore, a clear image in which the endoscopic image is distinctly separated from the marginal dark portion covered by the visual field mask image can be readily obtained without the need for the difficult work of sticking the visual field mask to the imaging surface.

In accordance with the tenth embodiment, the inserting section which requires disinfection can be watertightly separated from the solid state imaging device which is sensitive to heat or the like. Therefore, a strong disinfection method such as the use of an autoclave which might damage electronic devices can be applied, and a great effect can be produced in preventing infection. In addition, if several kinds of inserting sections having different optical systems such as an oblique view system and a side view system, a single expensive imaging section can be used for various applications.

Figure 17:
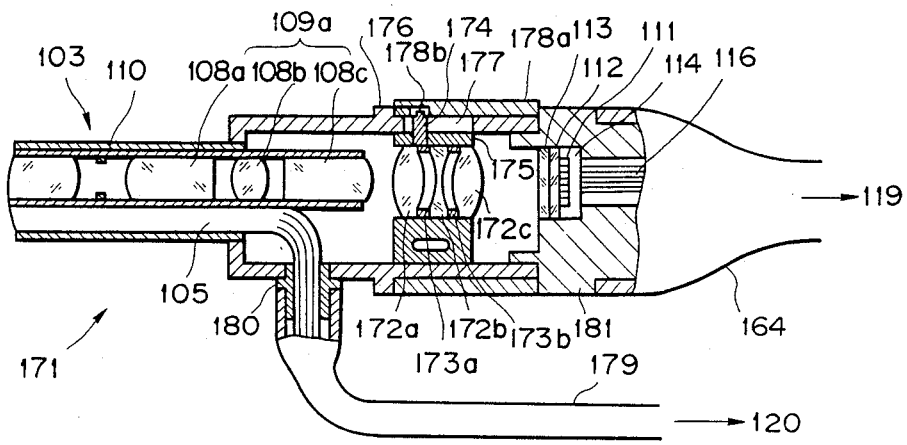
FIG. 17 is a partially sectional view of the essential portion of the control unit and associated circuitry of a rigid electronic endoscope according to an eleventh embodiment of the present invention.

FIG. 17 is an illustration, with essential portions cut away, of the operating section and associated portions of a rigid video endoscope according to an eleventh embodiment of the present invention.

In the eleventh embodiment, focusing lenses 172a, 172b and 172c together with spacer tubes 173a and 173b are fixed to a slidable tube 175 which has a pin 174 projecting from its outer periphery in an intermediate position between the final-stage relay lens group 109a and the solid state imaging device 111 so that the sliding tube 175 can be moved back and forth along the optical axis within an operating section 176. The pin 174 is inserted into an axially extending and linearily formed opening 177 provided in a side portion of the operating section 176, and extends into a cam groove 178b formed in the inner periphery of a cam tube 178a which is rotatably engaged with the outer periphery of the operating section 176 so that the pin 174 can slide with respect to both the linear opening 176 and the cam groove 178b. A light guide connector 180 which is connected to one end of a light guide cable 179 is fixed to the side wall of the operating section 176 at an axially forward position thereof. The light guide 105 passes through the light guide connector 180 and extends to the optical-line plug 120 which is provided at the rear end of the light guide cable 179. The proximal end of the operating section 176 is detachably connected to an imaging section 181 which stationarily holds the board 114 containing the solid state imaging device 111 to which the infrared cutoff filter 113 and the protection filter 112 are bonded. The rear end of the imaging section 181 in turn is connected to the cable 164 which includes the signal lines 116 extending from the board 114.

With this arrangement, if the distance between an object and the objective lens system varies greatly, the cam tube 178a can be rotated to cause the pin 174 to slid in the cam groove 178b and the linear opening 177, thereby causing the focusing lenses 172a, 172b and 172c to travel together with the slidable tube 175 within the operating section 176 so that an endoscopic image is constantly focused onto the imaging surface of the solid state imaging device 111. This provides a clear image in which the endoscopic image is distinctly separated from the marginal dark portion covered by the visual field mask image. In addition, since there is no need to incorporate the visual field mask 110 in the operating section 176, the structure of the operating section 176 is simplified. Furthermore, since the focusing lenses 172a, 172b and 172c can be disposed as close to the relay lens group 109a as possible, the distance between the relay lens group 109a and the solid state imaging device 111 can be shortened and thus the operating section 176 can be miniaturized.

Figure 18:
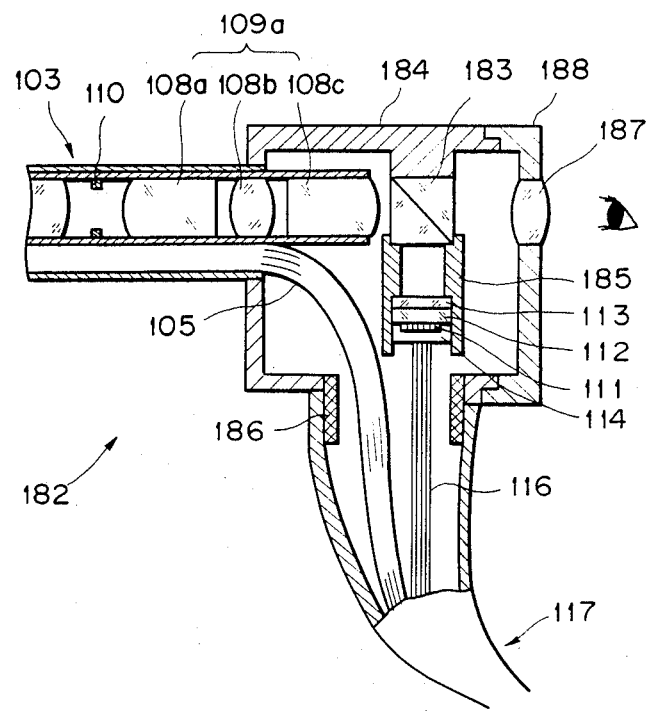
FIG. 18 is a partially sectional view of the essential portion of the control unit and associated circuitry of a rigid electronic endoscope according to a twelfth embodiment of the present invention.

FIG. 18 is an illustration, with the essential portions cut away, of the operating section and associated portions of a rigid video endoscope according to a twelfth embodiment of the present invention.

In this embodiment, a beam splitter 183 is adhesively fixed to an inner wall of an operating section 184 behind the final-stage relay lens group 109a to refract a portion of light rays transmitted through the relay lens system at right angles to the optical axis. An imaging section 185 stationarily holds the board 114 containing the solid state imaging device 111 to which the infrared cutoff filter 113 and the protection filter 112 are bonded, and is located with respect to the beam splitter 183 so that light rays separated by the beam splitter 183 are focused onto the imaging surface of the solid state imaging device 111. The signal lines 116 connected to the board 114 together with the light guide 105 extend into the cable 117 which is connected to a connector 186 mounted to a side wall of the operating section 184. An eyepiece unit 188, which holds an eyepiece lens 187 on the optical axis passing through the relay lens group 109a and the beam splitter 183, is connected to the rear end of the operating section 184.

With this arrangement, since there is no need to dispose the visual field mask 110 between the relay lens group 109a and the beam splitter 183, the distance therebetween can be sufficiently shortened. Since there is no need to dispose the visual field masks 110 between the beam splitter 183 and the solid state imaging device 111 or between the beam splitter 183 and the eyepiece lens 187, the operating section 184 can be simplified in structure and reduced in size. In addition, the incorporation of the visual field mask 110 within the relay lens system enables production of a clear image in which the endoscopic image is distinctly separated from the marginal dark portion covered by the visual field mask image.

Figure 19:
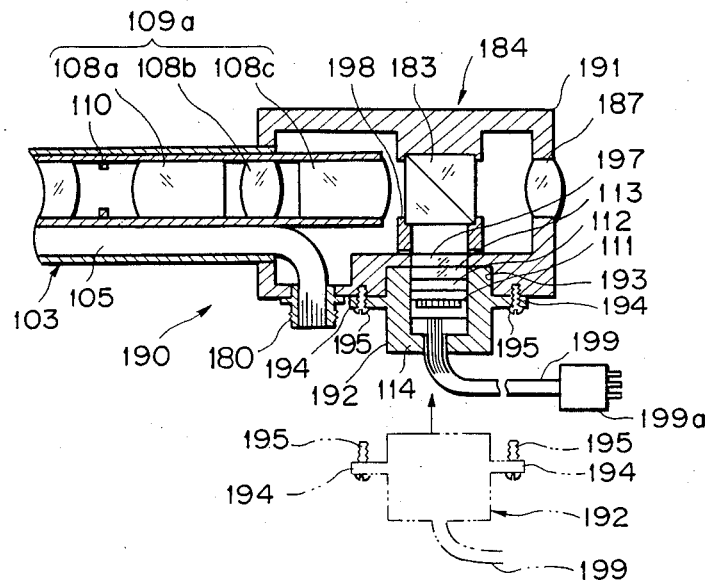
FIG. 19 is a diagrammatic, partially sectional view of the essential portion of a rigid video endoscope according to a thirteenth embodiment of the present invention.

FIG. 19 is an illustration, with the essential portions cut away, of a rigid video endoscope according to a thirteenth embodiment of the present invention, in which the rigid video endoscope is indicated generally at 190.

The rigid video endoscope 190 is a modified version of the endoscope shown in FIG. 18 in that its imaging means can be detached.

A frame 191 which constitutes a part of the operating section 184 is provided with the connector 180 which holds the light entrance end of the light guide 105. The light guide cable 179 shown in FIG. 17 can be connected to the connector 180.

A recess 193 for receiving an imaging unit 192 such as is shown in FIG. 19 is formed in the portion of the frame 191 that opposes the optical path refracted by the beam splitter 183. The imaging unit 192 is fitted into the recess 193, and screws 195, which are mounted in a flange 194 of the imaging unit 192, are screwed into corresponding internally threaded holes formed in the frame 191 so that the imaging unit 192 is secured to the frame 191.

An opening is formed in the portion of the frame 191 that has the recess 193, and a transparent plate 197 is fitted into the opening to endow the frame 191 with an airtight and watertight structure.

A light blocking hood 198 surrounds the optical path along which light rays are conducted from the beam splitter 183 to the imaging unit 192. A signal cable 199 connected to the solid state imaging device 111 extends from the imaging unit 192, and the distal end of the signal cable 199 is provided with a signal connector 199a.

This embodiment can also be used, with the imaging unit 192 removed therefrom, if there is no need to provide a visual display at a monitor.

If the endoscope 190 needs to be cleansed or sterilized, the portions other than the imaging unit 192 can be subjected to high temperature sterilization.

Figure 20:
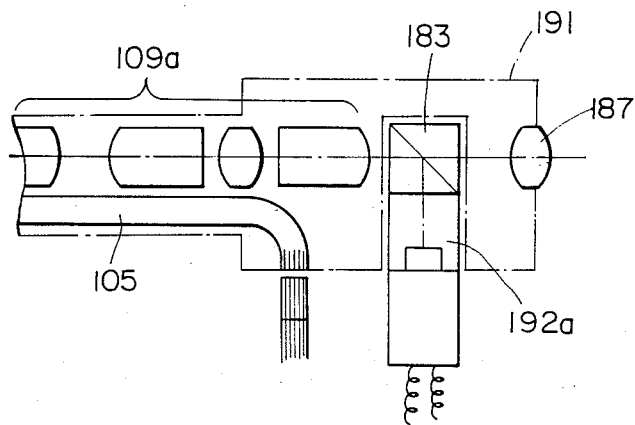
FIGS. 20 and 21 are diagrammatic, partially sectional views of the essential portion of a modification of the thirteenth embodiment of the present invention.
Figure 21:
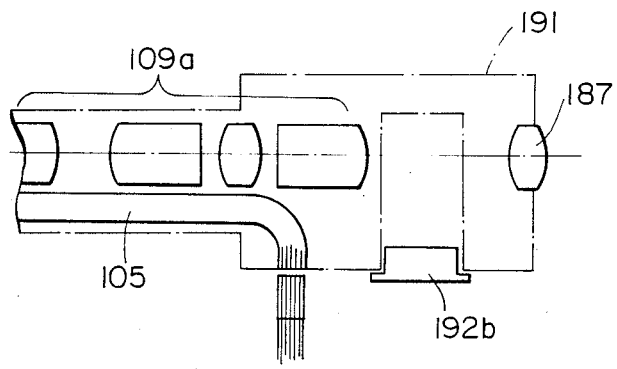

FIGS. 20 and 21 illustrate a modification of the thirteenth embodiment of the present invention. Each of these modification is provided with an imaging cassette 192a which integrally incorporates the beam splitter 183 and the imaging unit 192 which are shown in FIG. 19. The imaging cassette 192a is detachably mounted to the frame 191 of the rigid video endoscope 190. When the imaging cassette 192a is mounted, the beam splitter 183 is located on the optical axis of an optical image transferred through the relay lens system. Accordingly, light reflected from the object to be observed is separated into two beams by the beam splitter 183. One of the beams is made incident upon the solid state imaging device 111, and the output of the solid state imaging device 111 is displayed at a monitor (not shown). This enables simultaneous performance of observation through the monitor and visual observation through an eyepiece lens 298.

If the imaging cassette 192a is not used, it is detached from the frame 191 and, as shown in FIG. 21, a cassette mounting port is covered by a lid member 192b. Therefore, since the beam splitter 183 is also removed from the observation optical path, the quantity of light can be fully utilized for observation through the viewfinder.

Figure 22:
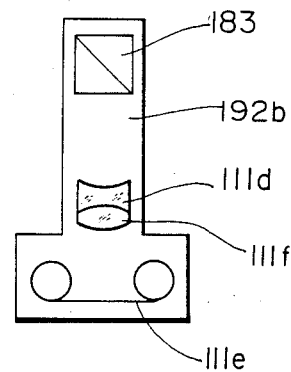
FIG. 22 is a schematic illustration of a cassette for incorporation in the thirteenth embodiment shown in FIG. 20, the cassette functioning as a still camera.

As shown in FIG. 22, the imaging cassette 192a may be replaced with a cassette 192b which functions as a still camera 111f having a dark box provided with a photographing lens 111d and a film 111e. This arrangement enables photographing of an object to be observed.

In addition, the infrared cutoff filter 113 may be removed the front of the solid state imaging device 111 of the imaging cassette 192a of FIG. 20, and illumination infrared light emitted from an infrared light source may be conducted into the light guide 105. With this arrangement, it is possible to easily perform observation employing infrared light from the infrared light source.

Figure 23:
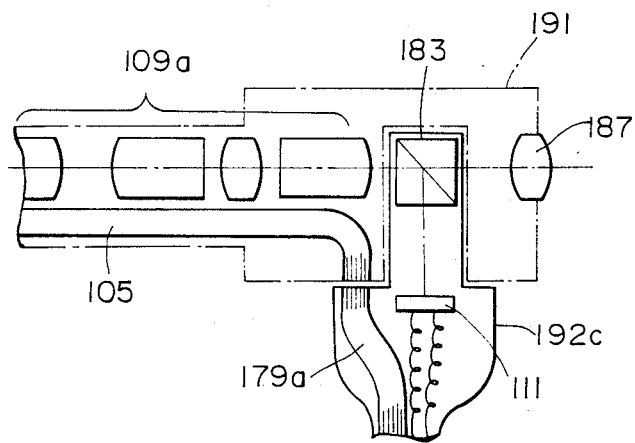
FIG. 23 is a diagrammatic, partially sectional view of the essential portion of yet another modification of the thirteenth embodiment.

FIG. 23 illustrates yet another modification of the thirteenth embodiment. In this modified form, a cassette 192c similar to the cassette 192a shown in FIG. 20 incorporates a connecting light guide 179a for conducting illumination light from a light source (not shown) to the light guide 105. At the same time that the cassette 192c is attached to or detached from the frame 191, the illumination light source can be connected to or disconnected from the light guide 105.

When the TV camera and the light guide are to be disconnected for storage or sterilization of the endoscope, two steps of time-consuming operations have heretofore been needed. However, this arrangement enables such a disconnecting operation in one step only.

Each of the aforesaid embodiments is of the type which is arranged to allow observation of an object which is located in the direction parallel to the axis of the inserting section. However, as shown in FIG. 24, the distal end portion of the present endoscope may be arranged to allow observation of an object which is located in an slanting direction, that is, at an angle $\alpha$ of less than 90° with respect to the axial direction of an inserting section 201.

Figure 24:
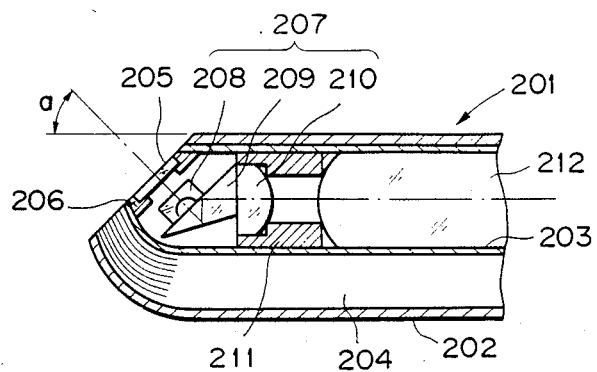
FIG. 24 is a diagrammatic sectional view of the essential portion of an inserting section according to a fourteenth embodiment of the present invention.

In the fourteenth embodiment shown in FIG. 24, a lens tube 203 is eccentrically disposed in a rigid external tube 202, and a light guide 204 is inserted into the space between the inner periphery of the external tube 202 and the outer periphery of the lens tube 203.

The end portions of the external tube 202 and the lens tube 203 are formed into a slanting cut-away hemispherical shape. The light exit face of the end of the light guide 204 faces that cut surface, and a cover glass 205 is fitted into the lens tube 203 at the cut-off end thereof by means of a cover glass mounting member 206. A lens 208, a prism 209 and a lens 210 which together constitute an objective lens system 207 are disposed behind the cover glass 205 in the interior of the lens tube 203. The lens 210 is mounted to the inner periphery of the lens tube 203 by means of a lens frame 211, and the prism 209 is adhesively secured to the lens 210 at the front surface thereof on the optical axis, with the lens 208 being adhesively secured to the front surface of the prism 209.

The objective lens system 207 has a optical axis shown by a one-dot dashed line. The optical axis of the objective lens system 207 extends on its light-exit side in the direction parallel to the longitudinal axis of the inserting section 201, and a relay optical system 212 extends along this optical axis.

Although not shown, the axially rearward portion of the inserting section 201 has the same structure as is shown in, for example, FIG. 1. Detailed description thereof is therefore omitted.

Figure 25:
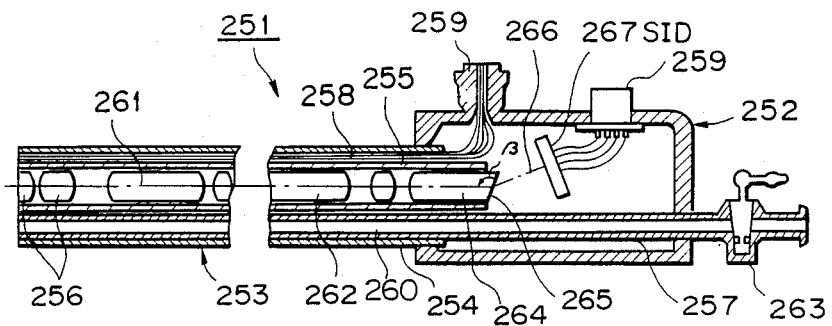
FIG. 25 is a diagrammatic sectional view, with parts omitted for sake of clarity, of a rigid video endoscope according to a fifteenth embodiment of the present invention.

FIG. 25 illustrates a fifteenth embodiment of the present invention, with several parts omitted for the sake of clarity.

A rigid video endoscope 251 includes an enlarged operating section 252, and a rigid external tube 254 projects from the enlarged operating section 252 at the axially front end thereof.

A lens tube 255 and a guide tube 257 the latter of which constitutes a forceps channel 260 are inserted in the external tube 254. A light guide 258 is inserted in the remaining axial space of the external tube 254 which is formed parallel to the axis of the guide tube 257. The proximal end of the light guide 258 within the operating section 252 is bent away from the guide tube 257, and is fixed to a light guide connector 259.

The lens tube 255 has an objective lens system 256 at its distal end, and a relay optical system 262 serving as an image transfer means is disposed on an optical axis 261 of the objective lens system 256. The relay optical system 262 extends through the inserting section 253 into the operating section 253.

The opening in the exit of the guide tube 257 is adjacent to the objective lens system 256 so that if a forceps is projected from the opening, it can be operated within the visual field. The proximal end portion of the guide tube 257 extends through the operating section 252 and projects outwardly from the rear end of the operating section 252. A stop cock 263 is provided in the guide tube 257 at a location near to the rear end thereof so that the guide tube 257 can be freely opened and closed.

A light exit surface 265 of a final lens element 264 which constitutes a part of the relay optical system 262 is formed at an obtuse angle $\beta$ exceeding 90° relative to the optical axis 261 rather than at right angles thereto. As shown in FIG. 25, the light exit surface 265 is formed as a cut surface which is inclined toward the forceps channel 256 so that the angle $\beta$ may reach its maximum value in a plane which contains the optical axis 261 and the axis of the forceps channel 256. Accordingly, the optical path 261 is bent at the light exit surface 265 to form an optical path 266 which extends in the direction away from the forceps channel 256. A solid state imaging device 267 is disposed on the optical axis 266 at the focus position of the relay lens element 265. The solid state imaging device 267 is electrically connected by signal cables to a signal connector receptacle 269 attached to the operating section 252.

In accordance with the above-described fifteenth embodiment, the optical axis 261 of the relay optical system 262 is bent at the light exit surface 265 in the direction away from the forceps channel 256 to thereby form the optical axis 266, and this makes it possible to dispose the solid state imaging device 267 without interfering with the forceps channel 256. Furthermore, since the imaging device 267 is disposed in an inclined state, the size of the operating section 252 is reduced as compared with a conventional arrangement in which a solid state imaging device is disposed at right angles to the optical axis 261.

It is to be noted that, although not shown, focusing can be performed by moving the solid state imaging device 267 back and forth along the optical axis 266. Alternatively, a focusing lens may be disposed on the optical axis 266 and focusing may be performed by moving the focusing lens back and forth along the optical axis 266.

Figure 26:
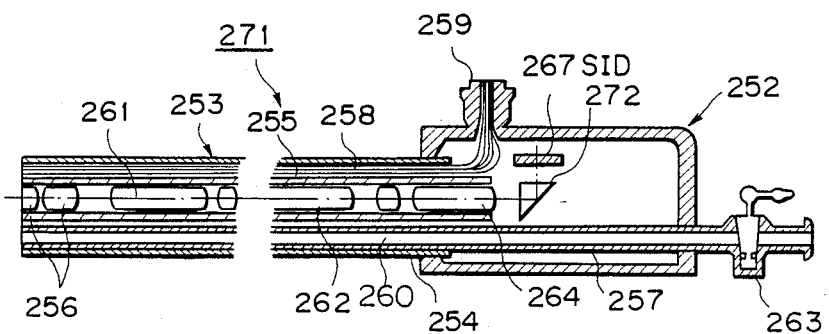
FIG. 26 is a diagrammatic sectional view, with parts omitted for sake of clarity, of a rigid video endoscope according to a sixteenth embodiment of the present invention.

FIG. 26 is a diagrammatic sectional view, with parts omitted for the sake of clarity, of a rigid video endoscope according to a sixteenth embodiment of the present invention.

In this sixteenth embodiment, the above-described light exit surface 265 for bending the optical axis 261 is not formed on the final relay lens element 264 which constitutes a part of the relay optical system 262, but a reflecting prism 272 is disposed on the optical axis 261 passing through the final relay lens element 264 to bend the optical axis 261 in a direction opposite to the forceps channel 256 and at right angles thereto, the solid state imaging device 267 being disposed at the focus position of the final relay lens element 264. Accordingly, the imaging surface of the solid state imaging device 267 is parallel to the optical axis 261.

It is to be noted that, although not shown, focusing can be performed by moving the solid state imaging device 267 and the reflecting prism 262 or the solid state imaging device 267 alone back and forth along the optical axis 261. (The signal connector receptacle 269 is omitted.)

Although not shown, a reflection mirror may be used in place of the reflecting prism 272. The angle and direction of bending of the optical axis 261 are not limited to those illustrated in this embodiment and may be arbitrarily selected in accordance with the internal structure of an individual rigid video endoscope.

Figure 27:
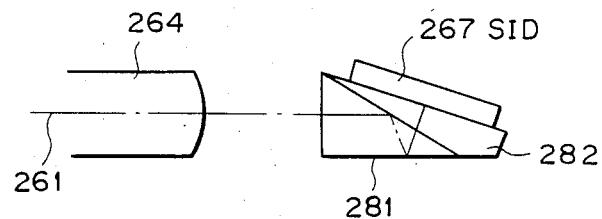
FIG. 27 is a schematic illustration of the essential portion according to a seventeenth embodiment of the present invention.

FIG. 27 is a schematic illustration of the essential portion of the optical system according to a seventeenth embodiment of the present invention.

In this seventeenth embodiment, an optical path changing prism 281 and an optical path correcting prism 282 are disposed behind the relay optical system 262 on the optical axis thereof, and the light exit surface of the prism 282 is made to coincide with the focus position of an optical image, the solid state imaging device 267 being mounted on the light exit surface of the prism 282. The solid state imaging device 267 is inclined with respect to the optical axis 261.

In accordance with the seventeenth embodiment, since the solid state imaging device 267 can be inclined at a location close to the optical axis 261, the whole apparatus can be reduced in size.

In each of the above-described fifteenth to seventeenth embodiments, the optical axis crosses the imaging surface of the solid state imaging device 267 at right angles. Although this arrangement is the most preferable one, the solid state imaging device 267 may be inclined with respect to the optical axis at an arbitrary angle other than 90°. In this case, the angle of inclination may preferably be determined within the range of the depth of focus or within a range in which electrical correction is enabled.

As shown in FIGS. 28 to 39, a detachable connecting means my be provided in front of the imaging device of each of the above-described rigid video endoscopes.

Figure 28:
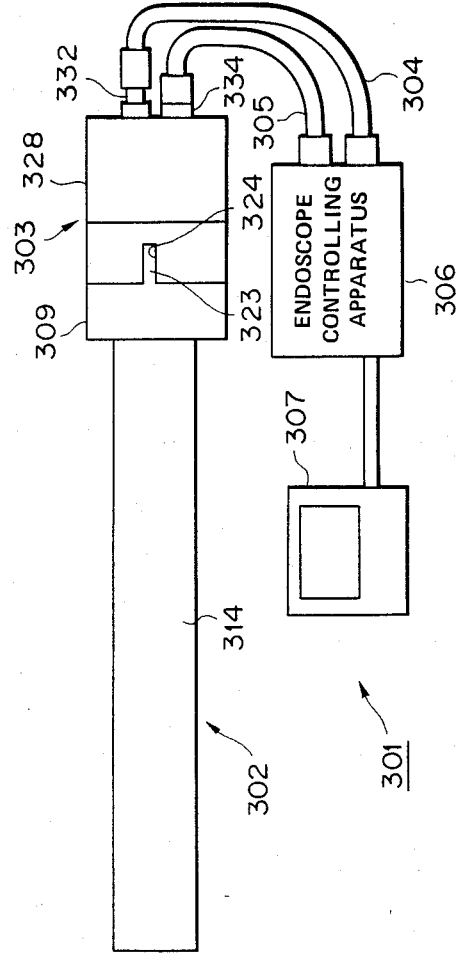
FIG. 28 is a schematic illustration of a rigid video endoscope according to an eighteenth embodiment of the present invention.

FIG. 28 is a schematic illustration of a rigid video endoscope according to an eighteenth embodiment of the present invention.

As illustrated, the rigid video endoscope system 301 to which the eighteenth embodiment is applied comprises a rigid endoscope body 302, an imaging-section body 303 detachably connected to the rigid endoscope body 302, an endoscope control apparatus 306 connected to the imaging-section body 303 through a light guide cable 304 and a signal cable 305, and a color monitor 307 for receiving video signals output from the rigid-endoscope control apparatus 306 to display a color image.

Figure 29:
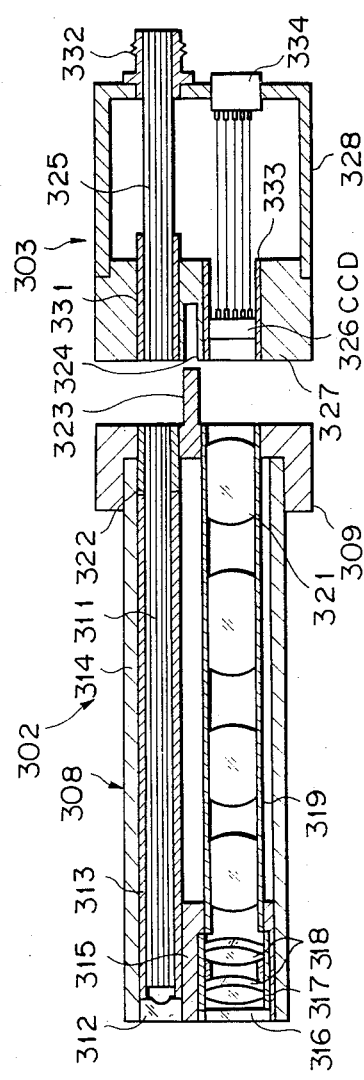
FIG. 29 is a sectional view of the essential portion of the eighteenth embodiment of the present invention.

As shown in FIG. 29, the rigid endoscope body 302 has an inserting section 308 having a small diameter and capable of being inserted into a hollow organ. The proximal end of the inserting section 308 is fixed to a proximal-end block 309 which has a large diameter and a stepped portion. A light guide 311 is inserted in the inserting section 308 for transferring illumination light incident upon the light entrance surface of the light guide 311 at the proximal end thereof and projecting the illumination light from the distal end. An illumination lens 312 is disposed in opposing relationship with the distal end surface of the light guide 311, and the illumination light transferred is projected onto an object from the illumination lens 312. In other words, an illumination optical system is formed by a combination of the light guide 311 and the illumination lens 312.

The light guide 311 which is covered by, for example, a protection tube 313 is inserted into a tubular case 314 made of metal which forms the inserting section 308.

A distal-end block 315 is fixed to the inner periphery of the tubular case 314 at the distal end portion of the insertion section 308. A through hole formed in the distal-end block 315 is closed by a cover glass 316, and an objective lens system 318 is fixed to a portion of the lens tube 14 adjacent to the cover glass 16 by means of a lens tube 317. Thus, an optical image focused by the objective lens system 318 is transferred rearwardly (to the right in FIG. 29) through a relay optical system 321 as an image transferring means which is fixedly disposed within a light blocking tube 319 for accommodating the relay optical system 321. An observation optical system is constituted by a combination of the objective lens system 318 and the relay optical system 321.

The proximal end portion of the relay optical system 321 is fixed in a through hole formed in the light blocking block 309 which is formed from a metal material or the like. The proximal end portion of the light guide 311 is fixed by a connector 322 in another through hole formed in the light blocking block 309.

Figure 30:
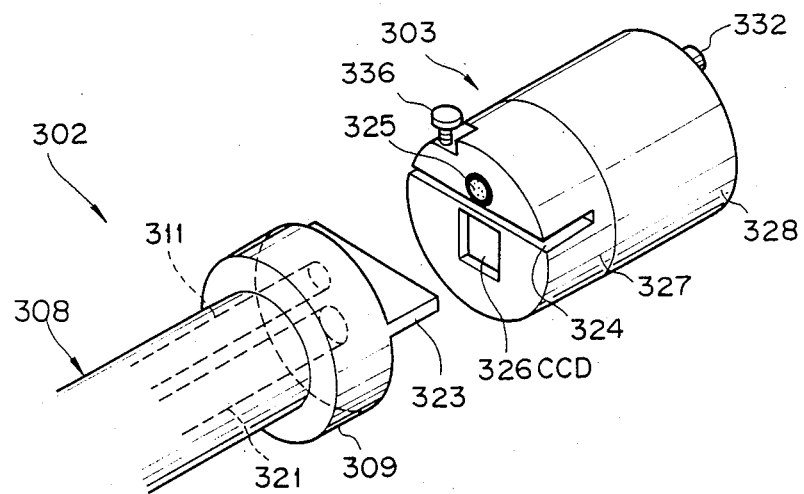
FIG. 30 is a diagrammatic perspective view of the essential portion of the eighteenth embodiment of the present invention, with non-visible portions illustrated for better understanding.

As shown in FIG. 30, a planar projection 323 which projects horizontally and rearwardly along the optical axis is formed on the axially rear end surface of the light blocking block 309, while a recess 324 for receiving the projection 323 is formed in the imaging-section body 303 at the axially front end thereof. Thus, a light connector means is formed which is capable of detachably connecting the rigid endoscope body 302 to the imaging-section body 303.

A light guide 325 is disposed on one side (the upper side in FIG. 30) of the recess 324 which is formed in the imaging-section body 303 and which serves as a guiding portion for connection (attachment), while a CCD 326 which serves as an imaging means is disposed on the other side (the lower side in FIG. 30) of the recess 324.

The center-to-center distance between the light guide 325 and the CCD 326 is equal to the center-to-center distance between the light guide 311 and the relay optical system 321 so that, when they are connected, the optical axes of the light guide 325 and the CCD 326 correspond to the optical axes of the light guide 311 and the relay optical system 321, respectively.

The imaging-section body 303 is comprised of a light blocking block 327 located axially forwardly and a frame portion 328 fixed to the axially rear end of the light blocking block 327, and the light blocking block 327 and the frame portion 328 have the same external diameter as the light blocking block 309 of the rigid endoscope body 302.

As shown in FIG. 29, the front end (the left-hand end) of the light guide 325 is fitted into a light blocking connector 331 and fixed in a through hole formed in the upper portion of the light blocking block 327, and the rear end (the right-hand end) of the light guide 325 is fixed by a light guide connector 332 at the rear end surface of the frame portion 328.

The CCD 326 is fixed by a light-blocking CCD mounting frame 33 in a through hole having a rectangular cross section which is formed in the light blocking block 327 at a position below the recess 324. The terminal of the CCD 326 is electrically connected through signal lines to a signal connector 334 at the rear end surface of the frame portion 328.

An illumination-light transmitting portion and an optical-image transmitting portion are disposed in vertically spaced-apart relationship at the proximal end portion of the rigid endoscope body 302 that is to be connected to the imaging-section body 303, and a light blocking projection 323 is formed between the illumination-light transmitting portion and the optical-image transmitting portion. Therefore, if, for example, illumination light which is to be made incident upon the proximal end of the light guide 311 is diffusively emitted toward the proximal end of the rigid endoscope body 302, the presence of the light blocking recess 323 positively prevents the diffused light from entering the connection joint of the optical-image transmitting portion below the recess 323.

In the imaging-section body 303 as well, an illumination-light transmitting portion and an optical-image transmitting portion are disposed in vertically spaced-apart relationship, and are mutually shielded against light penetration by the projection 323 inserted into the recess 324 of the light blocking block 327. Thus, illumination light is prevented from entering the imaging surface of the CCD 326.

After the projection 323 of the rigid endoscope body 302 has been fitted into the recess 324 of the imaging-section body 303, they can be locked by means of a fixing screw 336 disposed on one side of the light guide 325, as shown in, for example, FIG. 30. This ensures that they cannot mistakenly be detached from each other. (The fixing screw 336 may be disposed on each of the opposite sides of the light guide 325.)

In accordance with the eighteenth embodiment which is constructed as described above, the illumination-light side and the observation-light side are spaced apart from each other at the end surfaces to be joined together, and both sides are mutually shielded against light penetration by the light blocking projection 323. Should light be diffused at the connected end surfaces, the diffused light is positively prevented from entering the observation-light side by the projection 323.

Figure 31:
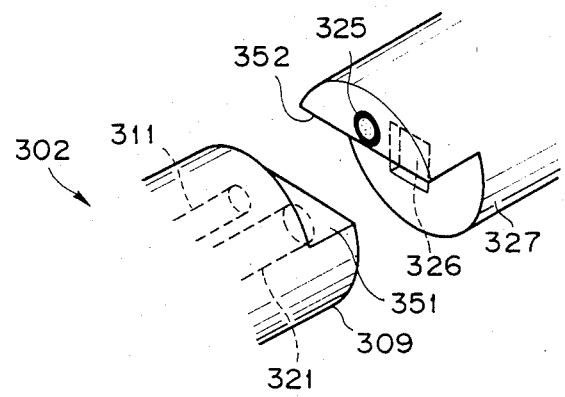
FIG. 31 is a diagrammatic perspective view of the essential portion of a nineteenth embodiment of the present invention, with non-visible portions illustrated for better understanding.

FIG. 31 shows the essential portion of a nineteenth embodiment of the present invention.

The nineteenth embodiment is a modified version of the above-described eighteenth embodiment in which stepped portions which are engageable with each other are provided instead of the recess 232 and the projection 323. Similar to the recess 232 and the projection 323 in the eighteenth embodiment, the stepped portions serve as guiding means for attachment and detachment and have the light blocking function of preventing diffused light from entering the CCD 326.

As shown in FIG. 31, the proximal end portion of the rigid endoscope body 302 is comprised of an upper portion including the light guide 311 and a lower portion including the relay optical system 321. In this embodiment, the lower portion may, for example, extend axially rearwardly to form a stepped portion provided with an axial surface 351 at an intermediate position between the light guide 311 and the relay optical system 321. On the other hand, the upper portion of the imaging-section body 303 extends axially forwardly to form a corresponding stepped portion provided with an axial surface 352.

The axial surface 352 is formed by cutting the light blocking block 309 so that the axial surface 352 may assume a light blocking function. The other axial surface 352 is formed by cutting the light blocking block 327 so that the axial surface 352 may assume a light blocking function. Accordingly, when the rigid endoscope body 302 and the imaging-section body 303 are joined together, the axial surface 351 prevents illumination light from entering the CCD 326 while the axial surface 352 prevents observation light from entering the illumination light side.

The construction of the remaining portion of the seventeenth embodiment is substantially the same as that of the eighteenth embodiment, and hence the seventeenth and eighteenth embodiments have a similar effect and function.

Figure 32:
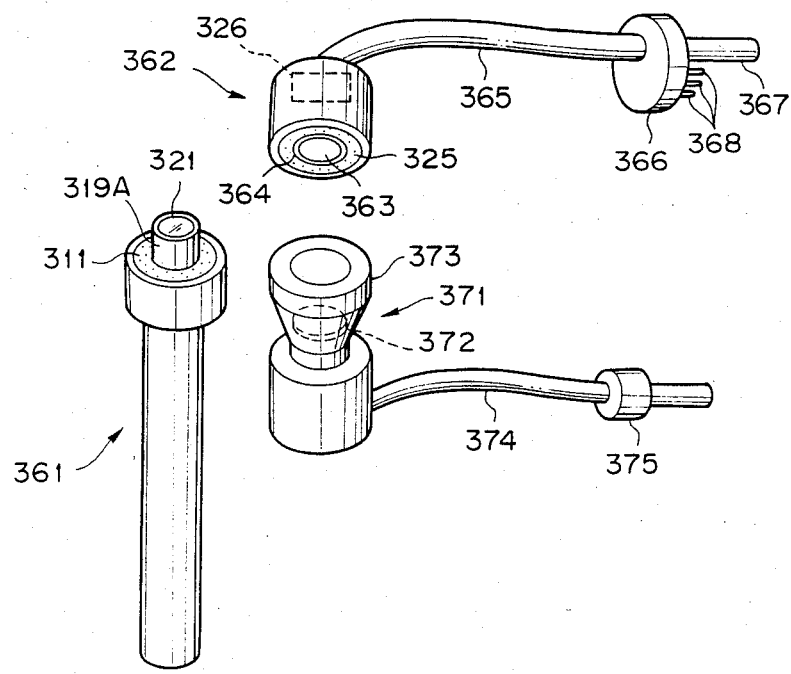
FIG. 32 is a diagrammatic illustration of a twentieth embodiment of the present invention.

FIG. 32 illustrates a twentieth embodiment of the present invention.

The rigid endoscope body 302 shown in FIG. 29 includes the objective lens system 318 and the relay optical system 321 which are inserted into the inserting section 308 eccentrically with respect to the axis thereof. In the twentieth embodiment, however, the objective lens system 318 and the inserting section 308 are inserted into a rigid endoscope body 361 along the axis thereof.

Figure 33:
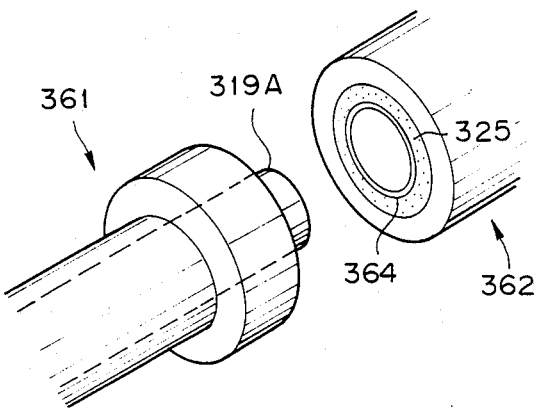
FIG. 33 is a diagrammatic perspective view of the essential portion of the twentieth embodiment of the present invention, with non-visible portions illustrated for better understanding.

In this twentieth embodiment, as shown in FIGS. 32 and 33, the relay optical system accommodating tube 319 projects from the proximal end surface of the light guide 311, and a projecting portion 319A of the relay optical system accommodating tube 319 forms a light blocking means which prevents the light of the light guide 311 disposed around the outer periphery of the tube 319 from entering the relay optical system 321. (The relay-optical system accommodating tube 319 is formed of a light blocking material.)

An imaging-section body 362 is provided with a recess 363 for receiving the projecting portion 319A, and a light blocking ring 364 constitutes a wall surface which defines the recess 363. A CCD 326 is disposed at an inward location in the recess 363 covered by the light blocking ring 364, and the imaging-section body 362 is attached to the rigid endoscope body 361 so that an optical image transferred through the relay optical system 321 is formed on the imaging surface of the CCD 326. An annular light guide 325 is disposed around the outer periphery of the light blocking ring 364 in opposing relationship with the light guide 311.

A universal cord 365 in which a signal cable of the light guide 325 and the CCD 326 are inserted extends from the rear end of the imaging-section body 362, and a connector 366 connected to one end of the cord 365 is attached to a control apparatus (not shown). Thus, illumination light is supplied to a light guide connector 367, and electrical contacts 368 are electrically connected to a signal processing system (not shown).

In this twentieth embodiment, as shown in FIG. 33, in addition to the imaging-section body 362, an eyepiece adapter 371 can be attached to the rigid endoscope body 361.

The eyepiece adapter 371, which is an applied form of the imaging-section body 362, is provided with an eyepiece 373 which accommodates an eyepiece lens 372 instead of the CCD 326. An operator can perform visual observation through the eyepiece 373. A light cable 374 in which a light guide is inserted extends from the eyepiece adapter 371, and a light guide connector 375 at the extended end of the light guide cable 374 can be connected to a light source unit or a light source device of a control apparatus.

In accordance with the twentieth embodiment, if the imaging-section body 362 is attached to the rigid endoscope body 361, video observation is enabled by using a monitor (not shown). If, instead of the imaging-section body 362, the eyepiece adapter 371 is attached to the rigid endoscope body 361, visual observation can also be performed.

In this embodiment, since the observation optical system and the illumination optical system are concentrically disposed, it is possible to arbitrarily set the orientation of an image to be observed by rotating the imaging-section body 362 with respect to the rigid endoscope body 361.

FIG. 34 shows the essential portion of a twenty-first embodiment of the present invention.

In the twenty-first embodiment, the light guide 311 and the relay optical system 312 are disposed in a rigid endoscope 381 in vertically spaced-apart relationship, and the light guide 325 and the CCD 326 are disposed in an imaging-section body 382 in vertically spaced-apart relationship, as in the eighteenth embodiment shown in FIG. 29.

Thus, the rear end of the rigid endoscope body 381 is connected to the imaging-section body 382, with cover glasses 383 and 384 interposed therebetween. As shown in, for example, FIGS. 34 and 35, these cover glasses 383 and 384 have non-transparent portions 385 and 386 which, respectively, horizontally extend between the light guide 311 on the upper side and the relay optical system 325 on the opposite side and between the light guide 325 on the upper side and the CCD 326 on the opposite side. Thus, light is prevented from entering from the upper side to the lower side or vice versa. The non-transparent portions 385 and 386 may be made by such a process as a two-color forming.

FIG. 36 shows the essential portion of a twenty-second embodiment of the present invention. The twenty-second embodiment employs polarizing plates 391 and 392 in place of the cover glasses 385 and 386 provided with the non-transparent portions 385 and 386, respectively.

As shown in FIG. 38, the polarizing plates 391 and 392 respectively have vertical and horizontal polarization axes which are orthogonal with each other. When light is incident upon each of the polarizing plates 391 and 392, light components parallel to the direction of polarization are transmitted through each of the polarization axes. Accordingly, axial surfaces 391A and 392A of the stepped portions of the polarizing plates 391 and 392, when they are engaged with each other, do not transmit light parallel to either of the polarization directions. Therefore, the axial surfaces 391A and 392A in combination serve as a light blocking portion 393 as shown in, for example, FIG. 37. The accommodation tube 319 which accommodates the light guide 311 and the relay optical system 321 is fixed to the polarizing plate 391 by a fixing plate 394. The light guide 325 and the CCD 326 are fixed to the polarizing plate 392 by a fixing plate 395. Therefore, the polarizing plates 391 and 392 can be connected by bringing the stepped portions of the polarizing plates 391 and 392 into engagement with each other, and the stepped portions serve as a light blocking portion (a non-transparent portion).

FIG. 39 shows a twenty-third embodiment of the present invention.

The twenty-third embodiment is a modified version of the previously-described twentieth embodiment, and a recess is formed in the relay optical system 321 at the proximal end of the rigid endoscope body 361, while a projecting portion is formed on the imaging section 362 at the corresponding position thereof. More specifically, the light blocking ring 364 projects from the axially front end of the imaging section 362, and the CCD 326 is disposed in the space within the light blocking ring 364. If the light blocking ring 364 is fitted into the recess of the rigid endoscope body 361, an optical image transferred through the relay optical system 321 is focused onto the imaging surface of the CCD 326.

The twenty-third embodiment has similar effect and function to those of the nineteenth embodiment.

If the distance (for example, indicated by symbol D in FIG. 37) between the illumination optical system and the observation optical system is made constant in each of the above-described embodiments, light connectors having interchangeability can be achieved.

It is to be noted that a fixing mechanism for connecting the rigid endoscope body to the imaging-section body may be constituted by screws, a bayonet mechanism or other known means.

As described above, in accordance with each of the seventeenth to twenty-second embodiments, when the imaging-section body is connected to the endoscope body having the illumination optical system and the observation optical system, a light blocking portion is formed between the both optical systems so that light from the illumination optical system can be prevented from entering the imaging device.

As shown in FIGS. 40 to 50, a rigid electronic scope (or endoscope) may be constructed so that a solid state image device is incorporated in an inserting section at the distal end portion thereof.

Figure 40:
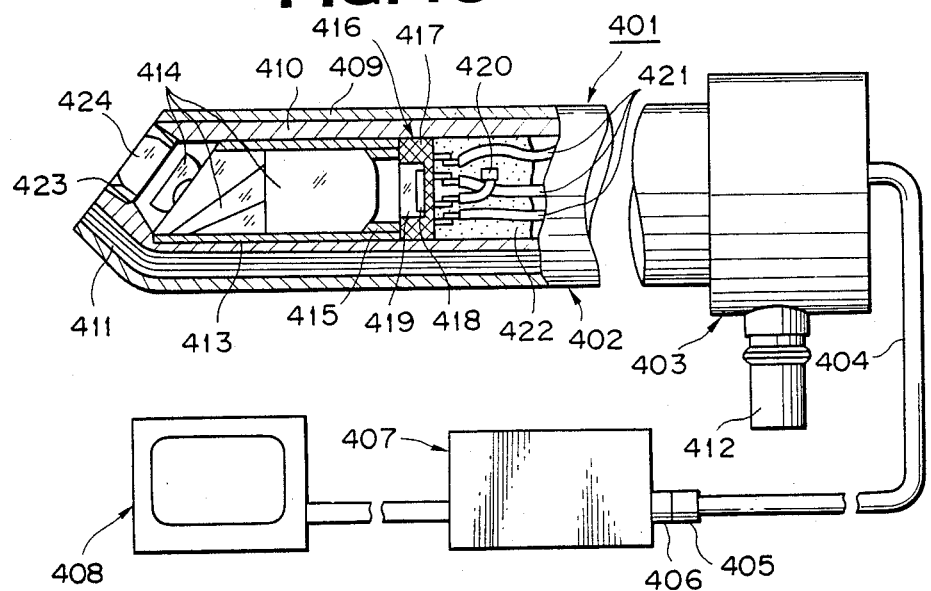
FIG. 40 is a diagrammatic illustration, with parts in section and other parts omitted for the sake of clarity, of an oblique-view type rigid electronic endoscope according to a twenty-fourth embodiment of the present invention.

Referring to FIG. 40 which shows a twenty-fourth embodiment, a rigid electronic scope 401 is comprised of an elongated inserting section 402 which can be linearily inserted into an portion such as a hollow organ to be observed; an enlarged operating section 403 which is connected to the proximal end of the inserting section 402; a cord 404 extending from the axially rear end of the operating section 403; and a connector 405 provided at the terminal end of the cord 404.

The connector 405 is connected through a connector receptacle 406 to a control apparatus 407 including a light source device and a video signal processing circuit. A color CRT monitor 408 as a display means is connected to the aforesaid control apparatus 407.

An external case 409, which constitutes a part of the inserting section 402, has a bottom portion which is bent forwardly upwardly at the distal end thereof, and the distal end of the external case 409 is obliquely cut away so that the bent portion of the bottom may be left. An internal tube 410 is inserted into the external case 409 in an eccentrical manner such that the internal tube 410 is kept in contact with an upper portion of the inner periphery of the external tube 409, and an internal tube 410 has a bottom portion which is bent forwardly upwardly at the distal end thereof and is obliquely cut away. A space having a crescent-shaped cross section is defined between the outer periphery of the internal tube 410 and the inner periphery of the external tube 409, and a light guide 411 is inserted into the crescent space. The proximal end portion of the light guide 411 which is inserted into between the space between the external tube 410 and the internal tube 409 in the inserting section 402 is bent in the operating section 403 and in turn is inserted into and fixed to a light guide connector 412 connected to the operating section 403 at one side thereof. One end surface of the light guide connector 412 serves as a light entrance face, and the illumination light of a light source device which will be described later is made incident upon the light entrance face through a light guide cable (not shown). The incident illumination light is projected forwardly obliquely from the distal end of the inserting section 402 that serves as a light exit end, and illuminates a portion to be observed.

A lens tube 413 is inserted into the internal tube 410, and an objective lens system 414 is adhesively fixed to the inner periphery of the lens tube 413 at the distal end thereof. A solid state imaging device 416 is disposed behind the objective lens system 414 on the optical axis thereof, with a spacer 415 interposed therebetween, the solid state imaging device 416 being fitted into the lens tube 413 perpendicularly to the optical axis of the rear element of the objective lens system 414. A prism-shaped recess is formed in a ceramic base 417 which is used as the base of the solid state imaging device 416 on the axially front side of the ceramic base 417 so that an imaging chip 418 may be perfectly buried in the recess. The imaging chip 418 which is fixed in the recess in the ceramic base 417 has a light receiving area (hereinafter referred to as an "imaging area") for photoelectric conversion, and is arranged to transfer electrical signals obtained from the imaging area to an amplifier 420 and associated rear-stage circuitry. The imaging chip 418 is airtightly covered by low melting point glass 491 charged into the recess in the ceramic base 417 so that the imaging chip 418 is thermally and physically protected. Signal lines 421 for transferring electrical signals as well as the amplifier section 420 are disposed behind the solid state imaging device 416, and are thermally and physically protected by a heat-resistant filling material 422. The signal lines 421 are connected through the operating section 403 to a cord 404 coated with Teflon having heat resistivity.

An objective cover glass 424 is fixed to an objective cover glass frame 423 on the optical axis of the front element of the objective lens system 414 and ahead thereof. The objective cover glass 424 is pressed into the objective cover glass frame 423 in such a manner that the outer periphery of the former is engaged with the inner periphery of the latter, and is fixed by an adhesive and pinching. The objective cover glass frame 423 which positively holds the objective cover glass 424 is fixed to the inner periphery of the internal tube 410 at the distal end thereof by press fitting and one or more of soldering, brazing and an adhesive or the like.

The objective cover glass 424 is formed of, for example, $Al_2O_3$ (alumina) single-crystal glass which can withstand exposure to high-temperature and high-pressure steam.

Figure 41:
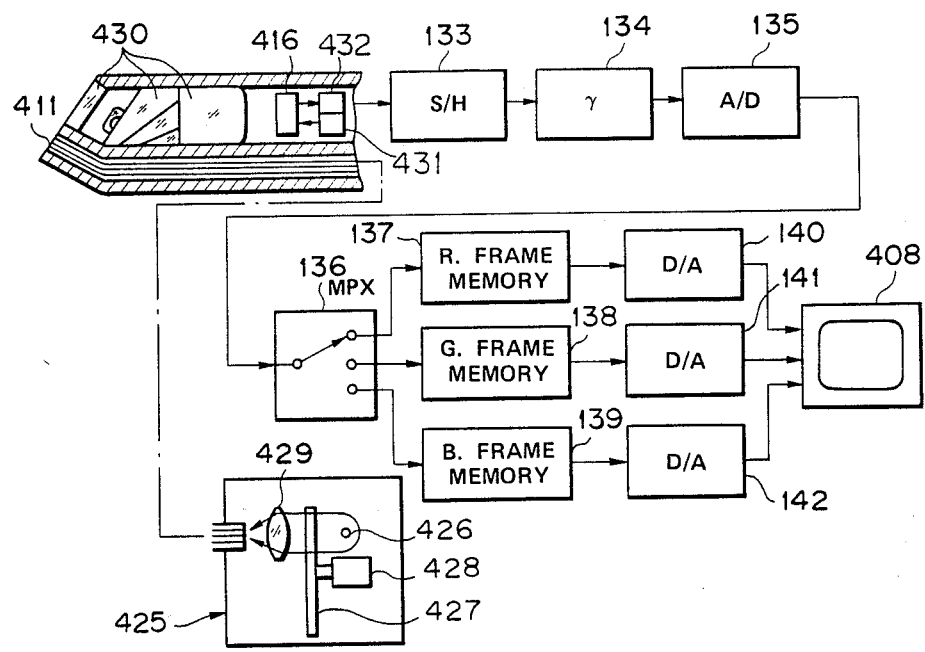
FIG. 41 is a block diagram illustrating the frame sequential video signal processing which is carried out in the twenty-fourth embodiment.

A light source device 425 disposed in the control apparatus 407, as shown in FIG. 41, is equipped with a light source lamp 426 and a rotary color filter 427 comprised of three primary color filters for transmitting red, green and green. The rotary color filter 427 is arranged to be rotated, for example, by the driving of a stepping motor 428. The illumination light of the light source lamp 426 is sequentially separated into wavelengths corresponding to red, green and blue by the rotary color filter 427, and is converged by a condenser lens 429. The thus-converged light enters the light guide 411 through the light guide connector 412 and passes through the light guide 411. The light is projected from the distal end of the inserting section 402 and illuminates a portion to be observed in a color-frame sequential manner.

Reflected light corresponding to each red, green and blue light from the portion to be observed is transmitted through an objective lens system 430 and is received by the imaging area of the imaging chip 418 buried in the solid state imaging device 416. Output signals from the imaging area of the imaging chip 418 are subjected to a video signal processing, as by a frame sequential system such as is shown in, for example, FIG. 41.

Since this processing system is similar to that shown in FIG. 13, description thereof is omitted.

The R, G and B signals passing through this processing system are input to the color CRT monitor 408 and the portion desired to be observed is displayed on the color CRT monitor 408.

Accordingly, an image of the portion to be observed can be smoothly recorded and reproduced by converting light signals into electrical signals by using the solid state imaging device 416 as an imaging means and by adopting a frame sequential system as a control system, and various image processings such as enlargement of an image and comparison of two images can be readily performed. Furthermore, as described previously, since the objective cover glass 424 is made of $Al_2O_3$ single-crystal glass, the present endoscope can be withstand repetitive sterilization with high-temperature and high-pressure steam, for example, at 135° C. at a pressure of 2 atm.

Figure 42:
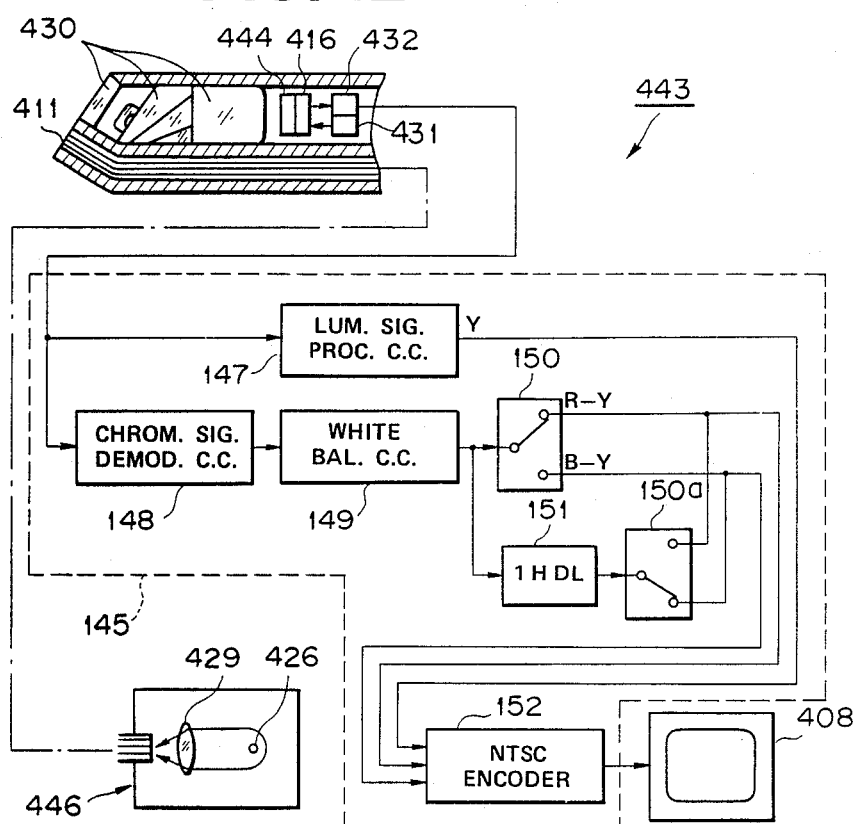
FIG. 42 is a block diagram illustrating the video signal processing using a built-in color filter system in the twenty-fourth embodiment.

FIG. 42 illustrates the diagrammatic construction of a rigid electronic scope system 433 of a built-in color filter type according to a modified form of the twenty-fourth embodiment.

This modified form comprises an optical system including the objective lens system 430 having the objective cover glass 424 and the objective lenses 414 which are disposed in the inserting section 402 at the distal end thereof and a color mosaic optical filter 444 disposed ahead of the solid state imaging device 416; and an electrical system including the solid state imaging device 416 and a preamplifier 431 or the like. The optical and electrical systems are arranged so that they can withstand repetitive sterilization with high-temperature and high-pressure steam, similarily to the optical and electrical systems shown in FIG. 40.

A mosaic-type processing circuit 445 and a light source device 446 such as are illustrated in FIG. 42 are incorporated in the control apparatus 407. The light source device 446 is essentially constituted by the light source lamp 426 and the condenser lens 429. White light emitted from the light source lamp 426 is converged by the condenser lens 429 and is transferred through a light guide cable (not shown) to the light guide connector 412. The light incident upon the light guide connector 412 is passed through the light guide 411 and projected from the distal end of the inserting section 402 to illuminate the portion desired to be observed.

White light reflected from the portion to be observed is transmitted through the objective lens system 430 and is made incident upon the color mosaic optical filter 444 which is disposed ahead of the solid state imaging device 416. The incident light is separated into three color elements of red, green and blue.

Light having each of the three color elements of red, green and blue is received by the imaging area of the imaging chip 418. Electrical signals of the imaging chip 418 which contain image information are subjected to a video signal processing, in a built-in color filter system such as is shown in, for example, FIG. 42.

This processing system is identical with that shown in FIG. 14, and description thereof is omitted.

Use of the above-described rigid electronic endoscope of an oblique view type that adopts the built-in color filter system facilitates imaging of a portion to be observed and recording and reproduction of the thus-imaged portion. Furthermore, as described previously, the present rigid electronic endoscope can withstand repetitive sterilization with high-temperature and high-pressure steam.

Figure 43:
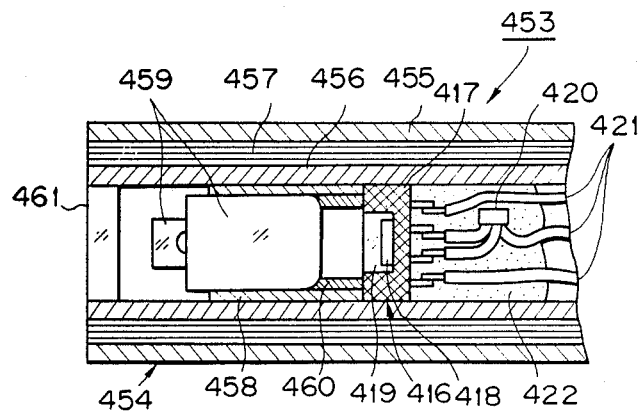
FIG. 43 is a diagrammatic sectional view of the essential end portion of a direct-view type rigid electronic scope according to a twenty-fifth embodiment.

FIG. 43 is a diagrammatic sectional view of a twenty-forth embodiment and illustrates the essential portion of the distal end portion of a direct-view rigid electronic scope which is related to the oblique-view rigid electronic scope 401 shown in FIG. 40.

The diagrammatic structure of an inserting section 454 is such that an internal tube 456 is inserted into an external tube 455, and a light guide 457 constituted by a fiber band forming a fiber band is inserted into the space defined between inner periphery of the external tube 455 and the outer periphery of the inner tube 456, an observation optical system and an electrical system being incorporated in the internal tube 456. A lens tube 458 for accommodating the observation optical system is inserted into the internal tube 456, and an objective lens system 459 which serves as an optical system for focusing a portion to be observed is fixed by an adhesive to the lens tube 458 at the distal end thereof. The electrical system constituted by the solid state imaging device 416, the amplifier section 420, the signal lines 421 and the like are disposed behind the objective lens system 459 with a spacer 460 interposed between the objective lens system 459 and the solid state imaging device 416.

Although not shown, electrical signals output from the electrical system through the intermediary of the optical system for focusing a portion to be observed are supplied through the signal lines 421 or the like in the inserting section 454 into the operating section 403 shown in, for example, FIG. 40. The electrical signals are transferred from the rear end of the operating section 403 through the cord 404 to the control apparatus 407. The electrical signals are then subjected to a video processing in the control apparatus 407, and outputs from the control apparatus 407 are viewed as a picture at the color CRT monitor 408.

The objective window of the front end of the objective lens system 459 which constitutes the observation optical system of the rigid electronic scope 453 is closed by an objective cover glass 461. The objective cover glass 461 has substantially the same diameter as the inner diameter of the internal tube 456, and the outer circumferential surface of the objective cover glass 461 is fixed to the inner periphery of the internal tube 456 at the distal end thereof by an adhesive or pinching. Thus, the airtightness of the interior of the internal tube 456 is maintained by the objective cover glass 461.

The objective cover glass 461 is preferably made of $Al_2O_3$ (alumina) signal-crystal glass which has water resistance and good heat resistance.

The imaging chip 418 which constitutes the solid state imaging device 416 of the electrical system is buried in a recess formed in the ceramic base 417, and is airtightly covered by the low melting point glass 419 charged in the recess. The amplifier 420 and the signal lines 421 are covered by the heat resistance filling material 422.

The proximal end (not shown) of the inserting section 453 of the direct-view rigid electronic endoscope is connected to the control apparatus 407 and the color CRT monitor 408 as shown in, for example, FIGS. 40 and 41. Although there is a difference in mechanism between the oblique-view and the direct-view observation optical systems, this twenty-fifth embodiment is the same as the twenty-forth embodiment shown in FIG. 40 in that, if a frame sequential system is used, the electrical signals of the solid state imaging device 416 are subjected to an image processing in the control apparatus 407 to provide a visual display at the color CRT monitor 408. Therefore, with the twenty-fifth embodiment, it is possible to perform image processing such as recording and reproducing of an image of a portion to be observed.

As described previously, the objective cover glass 461 is preferably made of $Al_2O_3$ (alumina) signal-crystal glass so that it can withstand repetitive sterilization with high-temperature and high-pressure steam, for example, at 135° C. at a pressure of 2 atm.

Although not mentioned in the above description made in conjunction with FIG. 43, the direct-view rigid electronic scope can likewise be applied to a built-in color filter system as well as the frame sequential system.

The material of the objective cover glass provided at the observation optical system of the above-described rigid electronic scope is not limited to $Al_2O_3$ (alumina) glass and, for example, boro-silicated glass can be used as the material.

The aforementioned oblique-view and direct-view rigid electronic endoscope are not exclusive and only illustrative, and, for example, the above-described embodiment can be likewise applied to side-view rigid endoscopes.

In the above-described frame sequential system, by way of example, sequential illumination is performed by using illumination light containing each of wavelengths of red, green and blue, but, of course, light having another wavelength may be employed.

As shown in FIGS. 44 to 50 which illustrate a twenty-sixth embodiment, a rigid electronic scope having a solid state imaging device in an inserting section may be constructed so that the axial length of the inserting section may be changed.

Figure 44:
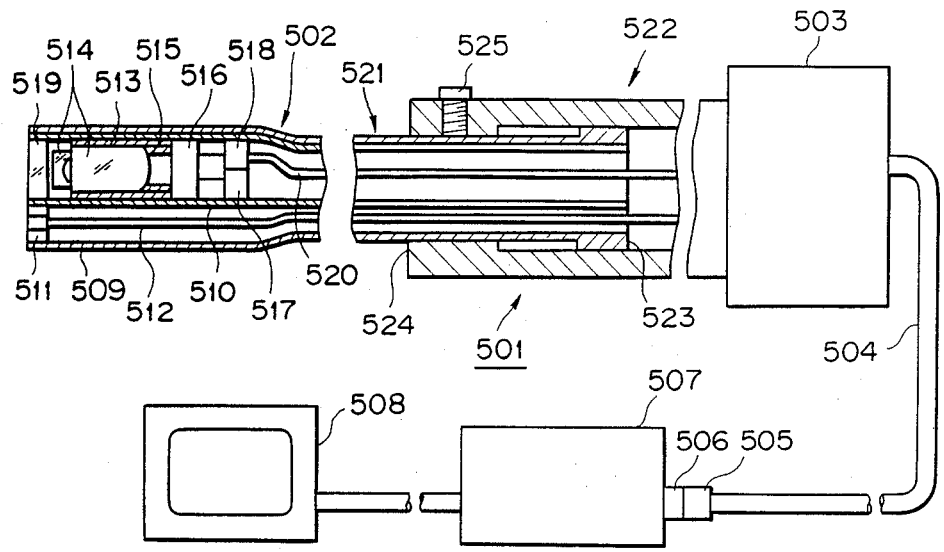
FIG. 44 is a diagrammatic illustration, with parts in section and other parts omitted for the sake of clarity, of a rigid electronic endoscope system according to a twenty-sixth embodiment.

Referring to FIG. 44, a rigid electronic endoscope 501 is comprised of an elongated inserting section 502 which can be linearly inserted into a portion such as a hollow organ to be observed; an enlarged operating section 503 which is connected to the proximal end of the inserting section 502; a cord 504 extending from the axially rear end of the operating section 503; and a connector 505 provided at the terminal end of the cord 504.

The connector 505 is connected through a connector receptacle 506 to a control apparatus 507 including a video signal processing circuit and the like. A color CRT monitor 508 as a display means is connected to the aforesaid control apparatus 507.

In the inserting section 502, an internal tube 510 is inserted into an external tube 509 in an eccentrical manner such that the outer periphery of the internal tube 510 is kept in contact with the upper portion of the inner periphery of the external tube 509, and a light emitting device 511 such as an LED which constitutes an illumination optical system is disposed in the space between the outer periphery of the internal tube 510 and the inner periphery of the external tube 509. An illumination power supply line 512 which conducts electrical power is connected to the light emitting device 511.

A lens tube 513 for accommodating an observation optical system is inserted into the internal tube 510, and an objective lens system 514 which serves as an optical system for focusing a portion to be observed is fixed by an adhesive to the lens tube 513 at the distal end portion thereof. The objective cover glass 519 which faces the portion to be observed is fixed to the lens tube 513 ahead of the objective lens system 514 on the optical axis thereof, and a solid state imaging device 516 is disposed behind the objective lens system 514 on the optical axis thereof, with a spacer interposed between the objective lens system 514 and the solid state imaging device 516. The solid state imaging device 516 is followed by a driving circuit 517 for driving the solid state imaging device 516 and a preamplifier 518 for amplifying output signals from the solid state imaging device 516. A signal line 520 is connected to the preamplifier 518 so that outputs therefrom may be supplied through the signal line 520 to form an observation electric system.

A rearward portion of the inserting section 502, through which the illumination power supply line 512 and the signal line 520 extend, is provided with an inner sleeve portion 521, and the inner sleeve portion 521 is inserted into an outer sleeve portion 522 which extends from the operating section 503 forwardly along the optical axis and which has a larger diameter than the inner sleeve portion 521. The inner sleeve portion 521 is disposed in the outer sleeve portion 522 for sliding movement forwardly and backwardly along the optical axis. Therefore, the axial length of the inserting section 502 can be varied.

An inner-sleeve projection 523 is formed around the outer periphery of the inner sleeve portion 521 at the rear end thereof, while an outer-sleeve projection 524 is formed around the inner periphery of the outer sleeve portion 522 at the front end thereof. Therefore, the inner sleeve portion 521 does not come off the outer sleeve portion 522.

Although not shown, an annular groove is formed in a portion of the inner periphery of the outer-sleeve projection 524 and, for example, an O ring is fitted into the annular groove so as to seal the gap between the outer-sleeve projection 524 and the inner-sleeve portion 521.

An internally threaded hole is formed, for example, at one location, in the front end of the outer sleeve portion 522 that has the outer-sleeve projection 524. A fixing screw 525 is screwed into the internally threaded hole. This constitutes a fixing means for fixing the inner sleeve portion 521 with respect to the outer sleeve portion 522 at a predetermined position thereof.

Light signals from the optical system for focusing a portion to be observed are converted into electrical signals by the solid state imaging device 516, amplified by the preamplifier 518, and output therefrom. The electrical signal output is supplied to the operating section 503 having the outer sleeve portion 522 through the signal line 520 which is inserted into the inner sleeve 521, and is input to the control apparatus 507 through the operating section 503.

Figure 45:
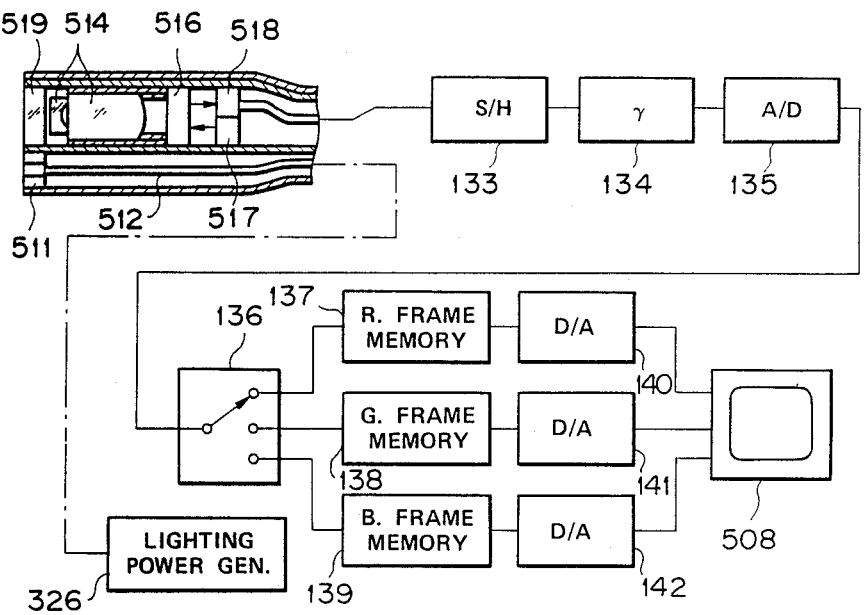
FIG. 45 is a block diagram illustrating the frame sequential video signal processing which is carried out in the twenty-sixth embodiment.

If the frame sequential system is adopted, the control apparatus 507 is arranged as shown in FIG. 45.

Referring to FIG. 45, an illumination power supply source 526 incorporated in the control apparatus 507 is connected through the illumination power supply line 512 to a light emitting device 511 constituted by, for example, LEDs. The light emitting device 511 is essentially constituted by LEDs for each emitting light having a different one of wavelengths corresponding to red (R), green (G) and blue (B). The light emitting device 511 is arranged to sequentially emit light of each of the wavelengths of the three colors by receiving electrical power from the illumination power supply line 426. The illumination light thus emitted illuminates a portion desired to be observed in a frame-sequential manner.

Reflected light corresponding to each red, green and blue light from the portion to be observed is transmitted through the objective lens system 514 and is received by the imaging area of an imaging chip (not shown) buried in the solid state imaging device 516. Output signals from the imaging area of the imaging chip are subjected to a video signal processing, as by a frame sequential system such as is shown in, for example, FIG. 45. The signal processing shown in FIG. 45 is the same as that shown in FIG. 13.

Figure 46:
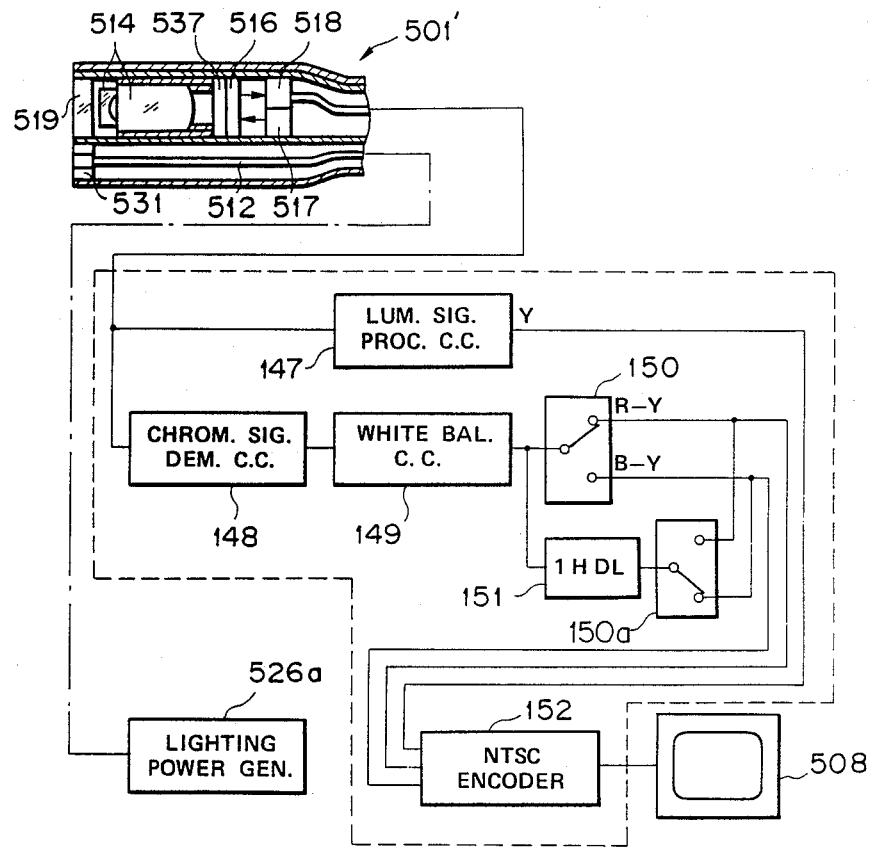
FIG. 46 is a block diagram illustrating the video signal processing using a built-in color filter system in the twenty-sixth embodiment.

A rigid video electronic scope of a built-in color filter type employs the illumination and signal processing systems which are arranged as shown in FIG. 46.

Referring to FIG. 46, an illumination power supply source 526a disposed in the control apparatus 507 is connected to a while light lamp 531 through the illumination power supply line 512. The lamp 531 emits white light by receiving electrical power from the illumination power supply line 526a, and illuminates a portion desired to be observed.

White light reflected from the portion to be observed is transmitted through the objective lens system 514, made incident upon a color mosaic optical filter 537 disposed ahead of the solid state imaging device 516 on the optical axis thereof, and separated into color elements of red, green and blue by the color mosaic optical filter 537.

The signal processing system connected to the solid state imaging device 516 has the same arrangement as that shown in FIG. 14.

A rigid electronic scope 501' according to the twenty-sixth embodiment shown in FIG. 46 includes the inner sleeve portion 521 to be inserted into a hollow organ or the like; the outer sleeve portion 522 which extends from the operating section 503 to provide support for the inner sleeve portion 521, the inner sleeve portion 521 being slideably fitted into the outer sleeve portion 522; and a mechanically fixing means for fixing the inner sleeve portion 521 with respect to the outer sleeve portion 522 at a desired position thereof, whereby the axial length of the inserting section 502 can be freely adjusted.

A light guide composed of a fiber bundle which is connected at one end thereof to a take-up reel in the operating section 503 may be employed in place of the illumination power supply line 512 and the light emitting device 511 or the lamp 531.

Although not shown, if the inner sleeve portion 521 has a large diameter, a tube which is smaller than the inner diameter of the inner sleeve portion 521 may be extended from the operating section 503 toward the axial front and inserted into the inner sleeve portion 522, without the inner sleeve portion 521 being fitted into the outer sleeve portion 522 for sliding movement forwardly and backwardly along the optical axis.

Figure 47:
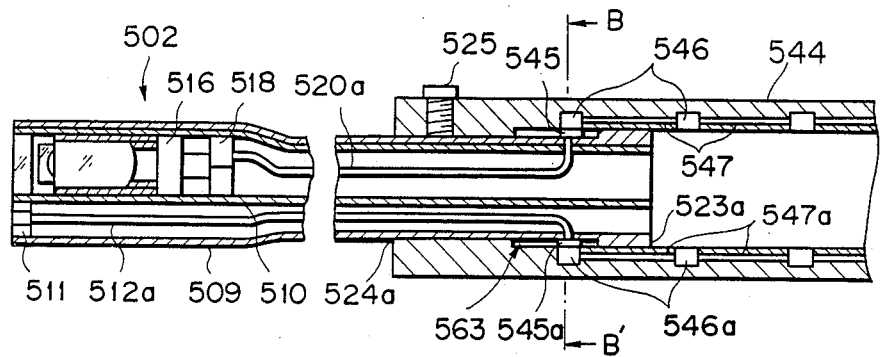
FIG. 47 is a diagrammatic sectional view, with portions omitted for the sake of clarity, of a modified form of the twenty-sixth embodiment in which the axial length of an inserting section thereof can be adjusted.

FIG. 47 diagrammatically shows a modified form of the twenty-sixth embodiment in which the axial length of an inserting section thereof can be varied.

An inner sleeve portion 563 formed at the rear end of the inserting section 502 is axially slideably fitted into an outer sleeve portion 544 having a larger diameter than an inner sleeve portion 553 which extends from an operating section (not shown) axially in the forward direction. An inner-sleeve projection 523a is formed around the outer periphery of the inner sleeve portion 553 at the rear end thereof, while an outer-sleeve projection 524a is formed around the inner periphery of the outer sleeve portion 544 at the front end thereof. Therefore, the inner sleeve portion 563 does not come off from the outer sleeve portion 544.

An internally threaded hole is formed, for example, at one location, in the front end of the outer sleeve portion 544 that has the outer-sleeve projection 524a, and the fixing screw 525 is screwed into the internally threaded hole. This constitutes a fixing means for fixing the inner sleeve portion 563 with respect to the outer sleeve portion 544 at a predetermined position thereof.

Electrical signals output from the solid state imaging device 516 are amplified by the preamplifier 518 and are transferred to a signal line 520a. The signal line 520a extends through the inner tube 510 in the inner sleeve portion 563, passes through a hole formed in the side wall of the inner sleeve portion 563 that is adjacent to the rear end thereof, and is in turn connected to an inner-sleeve contact 545 which projects from the outer periphery of the inner sleeve portion 553 ahead of the inner-sleeve projection 523a. The inner-sleeve contact 545 is adapted to come into contact with axially spaced-apart outer-sleeve contacts 546 which are buried in the outer sleeve portion 544 behind the outer-sleeve projection 524a and at arbitrary intervals. Adjacent ones of the outer-sleeve contacts 546 are connected in series by signal lines 547 which are buried in the outer sleeve portion 544.

Electrical power from an illumination power supply source in a control apparatus (not shown) is supplied to a series of illumination power supply lines 547 which are buried in the outer sleeve portion 544. The supply lines 547a are arranged to connect in series adjacent ones of outer-sleeve contacts 546a which are buried in the outer sleeve portion 544 at equal intervals and at positions corresponding to the the outer-sleeve contacts 546. The outer-sleeve contacts 546a are arranged to come into contact with an inner-sleeve contact 545a which projects from the outer periphery of the inner sleeve portion 553 at a position corresponding to the inner-sleeve projection 545. The inner-sleeve contact 545a is connected to an illumination power supply lines 512a in a hole formed in the inner sleeve portion 563. The illumination power supply line 512a is connected to a light emitting device 511 such as an LED which is disposed in the inserting section 502 at the distal end thereof.

Figure 48:
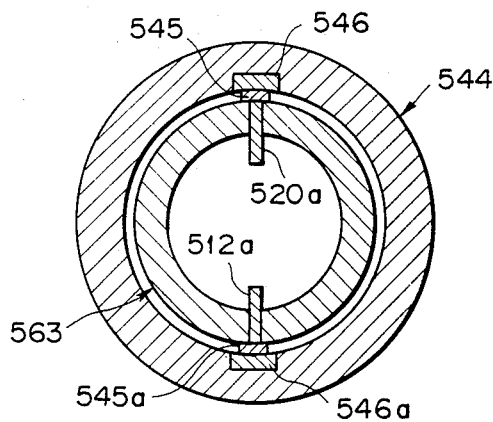
FIG. 48 is a sectional view taken along the line B—B' of FIG. 47.

FIG. 48 is a cross section taken along the line B—B' of FIG. 47, and illustrates the state wherein, in order to adjust the length of the inserting section 502 which is to be inserted, the inner sleeve portion 563 is slid with respect to the outer sleeve portion 544. The portions 563 and 544 are relatively fixed at positions at which the inner-sleeve contacts 545 and 545a are in contact with the outer-sleeve contacts 546 and 546a, respectively.

Thus, power can be supplied from an illumination power supply source (not shown) to, for example, the light emitting device 511, and electrical signals can be transferred from the solid state imaging device 516 to a video processing circuit.

Figure 49:
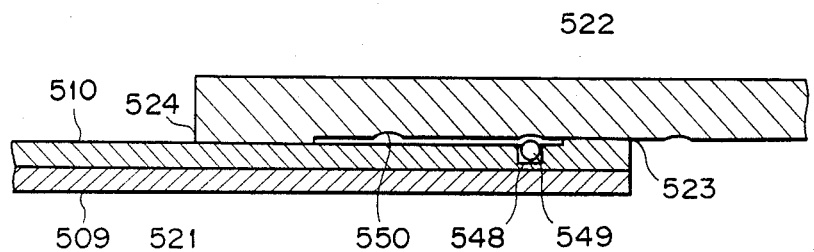
FIG. 49 is a sectional view of the essential portion of another modified form of the twenty-sixth embodiment in which the axial length of the inserting section thereof can be adjusted.

FIG. 49 is a sectional view of the essential portion of another modified form of the twenty-sixth embodiment in which the axial length of the inserting section thereof can be adjusted.

As illustrated, an annular groove 548 is formed in the inner sleeve portion 521 of the inserting section 502 around the inner periphery thereof and axially ahead of the inner-sleeve projection 523 which is formed around the outer periphery of the inner sleeve portion 521 at the rear end thereof. An 0 ring 549 formed of, for example, rubber is fitted into the annular groove 548. Annular recesses 550 are formed around the inner periphery of the outer sleeve portion 522 at arbitrary intervals behind the outer-sleeve projection 524 which are formed around the outer sleeve portion 522 at the front end thereof. The annular recesses 550 and the O ring 549 cooperate with each other to constitute a fixing means for stopping at an arbitrary position the relative sliding movement between the inner sleeve portion 521 and the outer sleeve portion 522.

Figure 50:
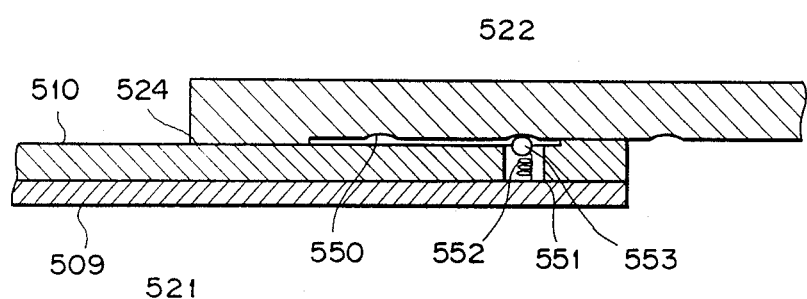
FIG. 50 is a view similar to FIG. 49, but showing a still another modified form of the twenty-sixth embodiment.

FIG. 50 shows still another modified form of the twenty-sixth embodiment in which the axial length of the inserting section thereof can be adjusted.

As illustrated in FIG. 50, a hole 551 is formed in the inner sleeve portion 521 axially ahead of the inner sleeve projection 523, and a steel ball 553 and a spring 552 are disposed in the hole 551 for engagement with a recess 550 formed around the inner periphery of the outer sleeve portion 522, thereby forming a fixing means.

It is to be noted that side-view or oblique-view rigid electronic endoscopes may assume the same structure as described above.

The mechanism for varying the axial length of the inserting section in each of the rigid electronic scopes described above in conjunction with FIGS. 44 to 50 can also be applied to rigid video endoscopes.

Figure 52:
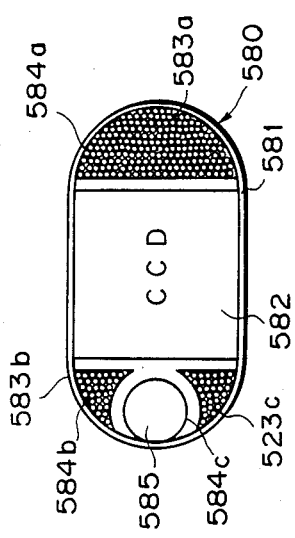
FIG. 52 is a view similar to FIG. 51, but showing a modified form of the arrangement shown in FIG. 51.
Figure 51:
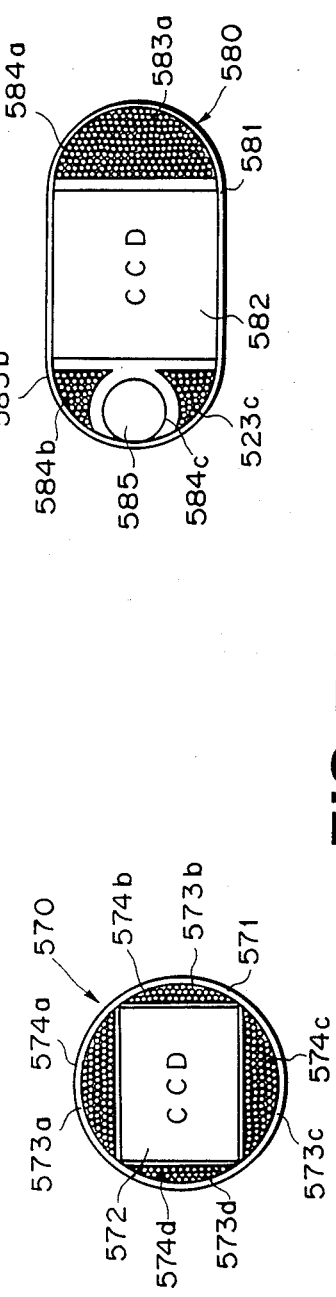
FIG. 51 is a front end view of the inserting section of a rigid embodiment endoscope according to the twenty-sixth embodiment and illustrates a solid state imaging device incorporated in the distal end portion of the inserting section and light guides around the imaging device.

In a rigid electronic scope which a accommodates solid state imaging device at the rear end of an inserting section, a light guide can be disposed as shown in FIGS. 51 and 52 to form an illumination optical system.

As shown in FIG. 51, a scope 570 has a tubular case 571 which is formed of a cylinder having a small diameter and an elongated configuration, and a CCD 572 having an imaging surface with a rectangular cross sectional form is disposed in the center of the tubular case 571 at the proximal end thereof. The rectangular CCD 572 having diagonal lines whose lengths are each approximately equal to the inner diameter of the tubular case 571 is disposed within the tubular case 571 having a circular cross section. Spaces 573a and 573d having a half moon-like cross section are formed between the four sides of the CCD 572 and the inner periphery of the tubular case 571.

Illumination light guides 574a to 574d each constituted by an optical fiber bundle are charged into the thus-formed spaces 573a to 573d. Thus, dead spaces can be effectively used. Since each of the spaces has a sufficient cross sectional area, light guide optical fiber bundles which ensure supply of a sufficient quantity of light can be disposed.

FIG. 52 shows a modified form of the arrangement shown in FIG. 51. A scope 580 according to the modified form is constituted by a tubular case 581 having an elongated tubular body with an oval cross section and a small diameter. A CCD 582 is disposed in the center of the tubular case 581, and a channel 585 for receiving an instrument such as a forceps is disposed on one side of the CCD 582. In the scope 580 having the above-described arrangement, spaces 583a to 583c are formed between the CCD 582 and the right-hand wall (as viewed in FIG. 52) of the tubular case 581 and between each of upper and lower portions of the insertion channel 585 and the inner surface of the left-hand wall of the tubular case 521. Illumination light guides 584a to 584c each constituted by an optical fiber bundle are charged into the spaces 583a to 583c, respectively. A sufficient quantity of illumination light can be obtained by arranging the light guides 584a to 584c in this manner.

In the above-described examples, the light guides are disposed in all the spaces formed between the tubular cases 571 and 581 and the CCDs 572 and 582, respectively. However, if the light guides are disposed in at least two of the spaces, a substantially sufficient quantity of light can be obtained.

Figure 53:
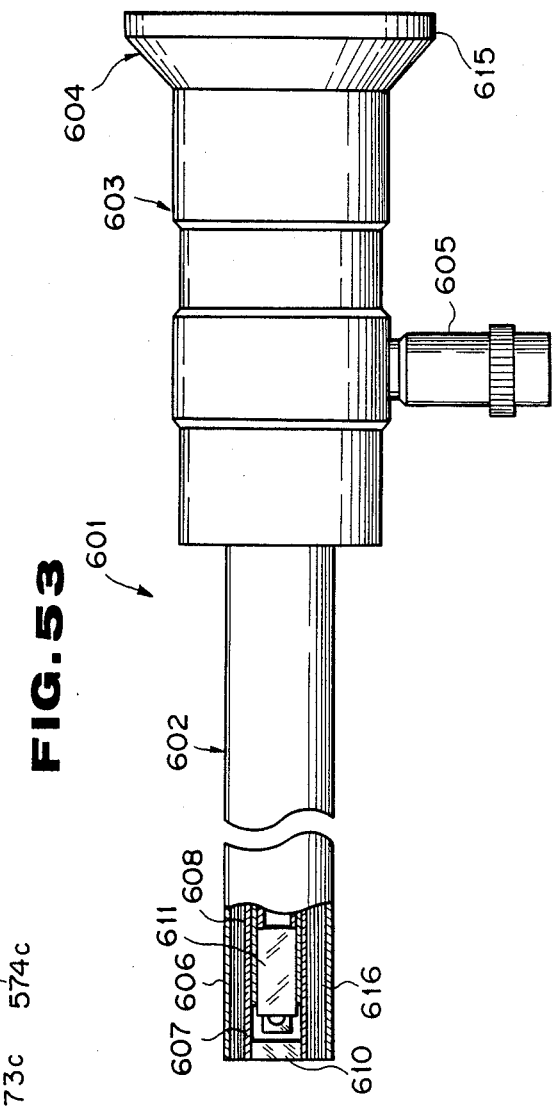
FIG. 53 is a diagrammatic illustration, with parts in section and other parts omitted for the sake of clarity, of a rigid endoscope according to a twenty-seventh embodiment of the present invention.
Figure 54:
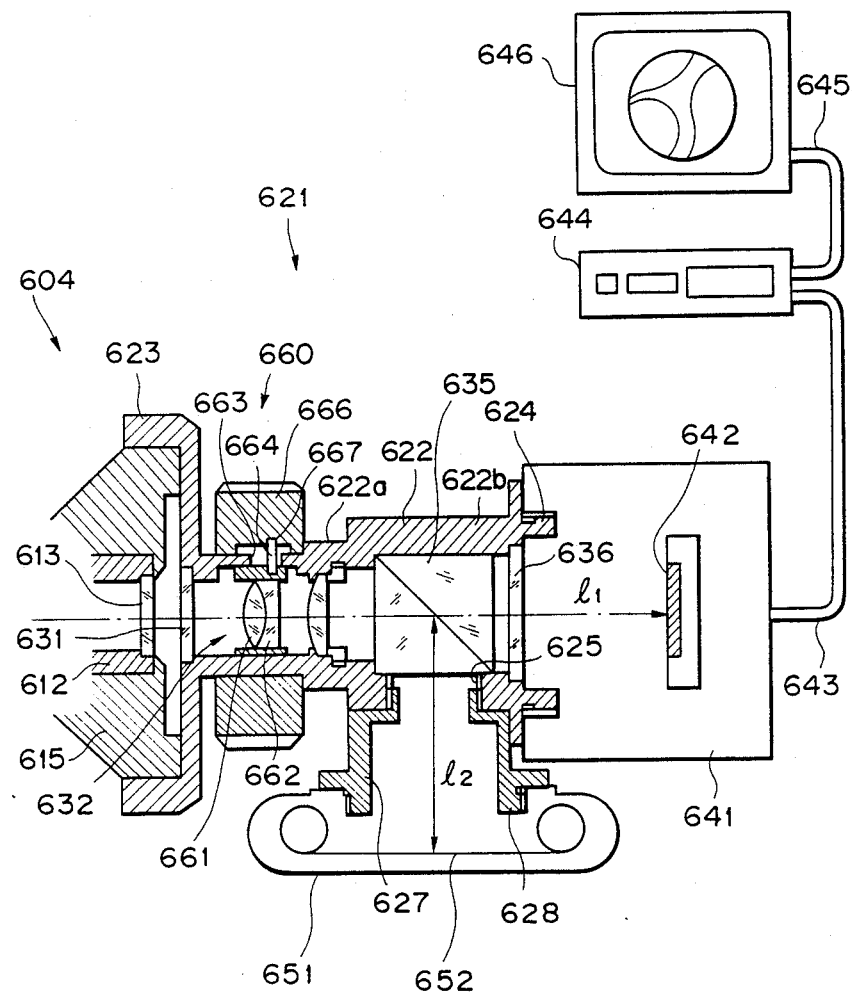
FIG. 54 is a diagrammatic partially sectional view of an optical adapter and its associated system which are attached to the eyepiece of the rigid endoscope according to the twenty-seventh embodiment.

An adapter device having the structure shown in FIG. 53 can be used as an adapter device which is attached to a rigid endoscope such as is shown in FIG. 54 for imaging purposes.

As shown in FIG. 54, a rigid endoscope 601 is constituted by an elongated rigid inserting section 602; an enlarged operating section 603 connected to the proximal end of the inserting section 602; and an eyepiece unit 604 connected to the rear end of the operating section 603. A light guide connector 605 is disposed on one side of the operating section 603.

An inner tube 607 is inserted into an outer tube 606 of the inserting section 602, and a lens tube 608 is inserted into the inner tube 607. An objective cover glass 610 is fixed to the inner periphery of the inner tube 607 at the proximal end thereof, and an objective lens system 611 is fitted into the internal tube 607 behind the objective cover glass 610. Furthermore, a relay lens system (not shown) for transferring an image of an object focused by the objective lens 611 to the eyepiece unit 604 is disposed in the internal tube 607 behind the objective lens system 611. As shown in FIG. 54, the eyepiece unit 604 is supported by an eyepiece frame 612, and has an eyepiece cover glass which opposes the rear end of the aforesaid relay lens system. An eyepiece 615, which progressively increases in diameter, is attached to the rear end of the eyepiece frame 612 at the outside thereof.

A light guide fiber 618 is inserted into the space between the internal tube 607 and an external tube 606. The light exit end of the light guide fiber 616 at the distal end thereof is vertically aligned with the distal ends of the internal tube 607 and the external tube 606. The proximal end of the light guide fiber 616 is bent and extended to the light guide connector 605 in the inserting section 603.

An endoscope optical adapter apparatus 621 having a structure such as is shown in FIG. 54 can be attached to the eyepiece 615 of the aforesaid rigid endoscope 601.

More specifically, the endoscope optical adapter apparatus 612 is provided with a substantially cylindrical adapter body 622, and the adapter apparatus 622 has a barrel portion 622a at the front end thereof and a beam splitter accommodating portion 622b at the rear end. A scope mount 623 is formed on the barrel portion 622a at the front end thereof, and the scope mount 623 can be connected to the eyepiece unit 604 by being fitted onto the eyepiece 615 of the eyepiece unit 604 of the rigid endoscope 601. On the other hand, a TV camera mount 624 is formed at the beam splitter accommodating portion 622b at the rear end thereof, and a TV camera 641 serving as an observation means can be connected to the TV camera mount 624 in a screwed manner. An opening 625 having, for example, a circular shape is formed in the beam splitter accommodating portion 622b at one side thereof, and the opening 625 is internally threaded. A still camera connecting member 627 having an approximately cylindrical shape has an externally threaded end portion which can be screwed into the internally threaded portion. The still camera connecting member 627 is connected to the opening 625 by screwing the externally threaded end portion into the internally threaded portion. A still camera mount 628 is formed at the end of the still camera connecting member 627 that is opposite to the adapter body 622, and a still camera 651 can be connected to the still camera connecting member 627 in a screwed manner.

An eyepiece cover glass 631 is mounted in the scope mount 623 in the center thereof in face-to-face relationship with the eyepiece cover glass 613 of the eyepiece unit 4. A focusing lens system 632 is disposed in the barrel portion 622a behind the cover glass 631, which system has an optical axis corresponding to the optical axis of the observation optical system of the endoscope. A beam splitter 635, which is accommodated in the beam splitter accommodating portion 622b, is disposed behind the focusing lens system 632, the beams splitter 635 serving to separate light beam from the eyepiece unit 604 into two beams. A cover glass mount 636 is attached to the TV camera mount 624 in the center thereof, and the beam transmitted through the beam splitter 635 passes through the cover glass 636 and falls upon, for example, a (solid state) imaging device 642 of the TV camera 641 which is connected to the TV camera mount 624. The imaging device 642 is disposed at the focus position of the focusing lens system 632.

The TV camera 641 is connected through a signal cable 643 to a camera control unit 644 in which outputs signals from the imaging device 542 are subjected to a video signal processing. The camera control unit 644 is connected to a TV monitor 646 through a signal cable 645. An image of an object imaged by the TV camera 641 is displayed on the TV monitor 646.

The beam reflected by the beam splitter 635 passes through the opening 625 formed in the beam splitter accommodating portion 622b on one side thereof as well as the still camera connecting member 627, and is formed on a film 652 which is placed in the still camera 651 connected to the still camera mount 628. The film 652 is disposed in the focus position of the focusing lens system 632.

In the above-described embodiment, the still camera 651 is not provided with a viewfinder or a focusing means.

In the above-described embodiment, an optical distance l1 between the beam separating position of the beam splitter 635 and the imaging device 642 of the TV camera 641 is equal to an optical distance l2 between the beam separating position of the beam splitter 635 and the sensitization position of the film 652 in the still camera 651.

The above-described embodiment further includes a focusing portion 660 which is disposed on the light entrance side of the beam splitter 635 for adjustment of focus of the TV camera 641 connected to the TV camera mount 624 and the still camera 651 connected to the still camera mount 628. More specifically, as shown in FIG. 54, a portion of the focusing lens system 632 serves as a focusing lens 661, and the focusing lens 661 is held by a focusing lens frame 662 which can be slid in the barrel portion 622a forwardly and backwardly along the optical axis. A slot 663 is formed in the barrel portion 622a along the optical axis, and provide communication between the interior and exterior of the barrel portion 622a. A pin 664 is disposed in an upright manner on the outer periphery of the focusing lens frame 662, and the pin 664 projects through the slot 663 to the outside of the barrel portion 622a. Therefore, the pin 664, that is, the focusing lens frame 662 can be moved along the slot 663 forwardly and backwardly along the optical axis. An operating ring 666 is fitted on the barrel portion 622a for rotation about the optical axis. A circumferential groove 667 is helically formed in the inner periphery of the operating ring 666 so that the pin 664 may engage with the groove 667. If the operating ring 666 is rotated, the pin 664 which is engaged with the groove 667 in the operating ring 666 is caused to move in the slot 664 in the barrel portion 622a along the optical axis so that focus is adjusted along the optical axis of the focusing lens 661.

The following is a description of the adapter apparatus 621 having the above-described arrangement and construction.

When a still photography is to be taken of an object image observed by the rigid endoscope 601, the scope mount 623 of the endoscope optical adapter apparatus 621 is connected to the eyepiece 604 of the rigid endoscope 601 and the TV camera 641 and the still camera 651 are connected to the TV camera mount 624 and the still camera mount 628, respectively. Then, the object image which has been imaged by the TV camera 641 is displayed on the TV monitor 646, and while the image displayed on the TV monitor 646 is being observed, the operating ring 666 of the focusing portion 660 of the adapter apparatus 621 is rotated to adjust focus. In the above-described embodiment, the beam passing through the focusing portion 660 is separated into two beams by the beam splitter 635, and the TV camera 641 and the still camera 651 are disposed at the respective focus positions of the thus-separated beams. Therefore, the TV camera 641 and the still camera 651 are focused simultaneously and similarly by a focusing operation of the focusing portion 660. Accordingly, when the image displayed on the TV monitor 646 is brought into focus, the still camera 65 is interlockingly brought into focus. Finally, in a state wherein the image displayed on the TV monitor 646 is focused, a shutter (not shown) of the still camera 651 is operated to take a still photograph of the object.

Since only the beam splitter 635 is used to separate light beam into the beam for TV camera 641 and the beam for still camera 651, either the TV camera 641 or the still camera 651 produces a reversed image. However, the reversed image taken by the TV camera 641 may be converted into a correct image by electrical correction (for example, by storing a freezed image in a frame memory and reading out the stored image in the order of scanning lines reverse to the order of storage). The reversed image taken by the still camera can be corrected by printing it as a further reversed image.

In this manner, since an operator can adjust focus of the still camera 651 while viewing the image displayed on the TV monitor 646, the operator can look into the viewfinder of the still camera 651 without a forced posture. This improves the operability of the system.

Since a still photography can be taken by the still camera 651 without a viewfinder, the weight and size of the still camera 651 can be reduced. In addition, a display device (not shown) which allows a visual observation at a location remote from the eyepiece unit 604 may be connected to the TV camera mount 624 in place of the TV camera 641, and the image observed by the eyepiece unit 604 may be transferred to the display device through an image guide fiber or the like. The operator can adjust focus by operating the focusing portion 660 while observing the image displayed on the display device.

The amount of exposure may be calculated from the output signals of the TV camera 641, and the aperture or shutter speed of the still camera 651 may be adjusted in accordance with the exposure information. A diaphragm may be disposed on the light entrance side of the beam splitter 635 in the endoscope optical adapter apparatus 621, and adjustment of the diaphragm may be performed while viewing the image displayed on the TV monitor 646.

The TV camera 641 connected to the TV camera mount 624 is not limited solely to the type which employs a solid state imaging device, and the type which uses an image pick-up tube may also be applied.

As a matter of course, the above-described construction may be applied to flexible endoscopes as well as rigid endoscopes.

As shown in FIGS. 55 to 62 which illustrate a twenty-eighth embodiment, a self-convergence type rod lens may be employed as an objective lens system.

Figure 55:
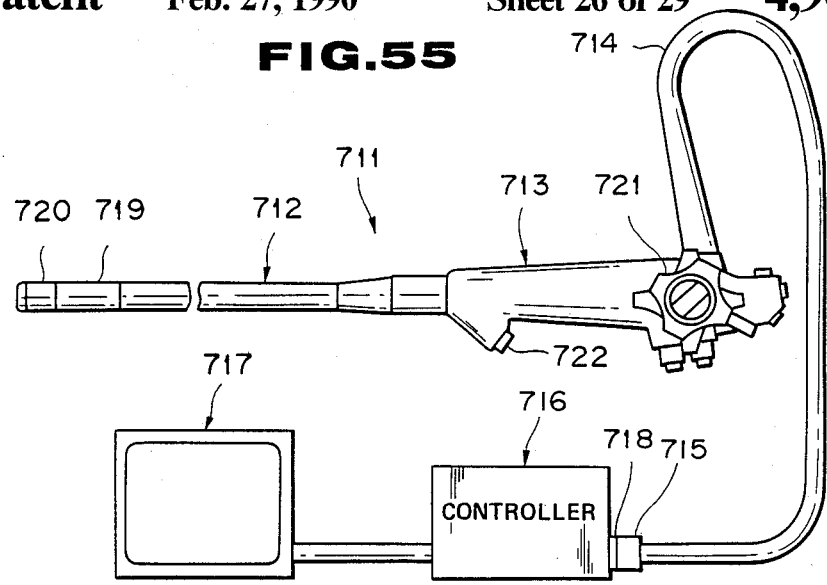
FIG. 55 is a diagrammatic illustration of a flexible electronic endoscope system according to a twenty-eighth embodiment.

Referring to FIG. 55, a flexible electronic endoscope 711 according to the twenty-eighth embodiment is provided with an elongated flexible inserting section 712, and a large diameter operating section 713 is connected to the proximal end of the inserting section 712. A flexible universal cord 714 may extend laterally from the rear end of the operating section 713, and a connector 715 is provided at the end of the universal cord 714. A control apparatus 716 which includes a light source device and a signal processing circuit is provided with a connector receptacle 718 capable of receiving the connector 715. The electronic endoscope 711 is adapted to be connected to the control apparatus 716 by connecting the connector 715 to the connector receptacle 718. A color monitor 717 serving as a display means can be connected to the control apparatus 716.

The distal end portion of the inserting section 712 has a rigid end portion 720 and a bendable portion 719 which is axially adjacent to the rear of the end portion 720. The operating section 713 is provided with a bending knob 721. The bending knob 713 can be rotated to bend the bendable portion 719 vertically and horizontally. The operating section 713 is provided with an insertion port 722 which communicates with an instrument channel defined in the inserting section 712.

Figure 59:
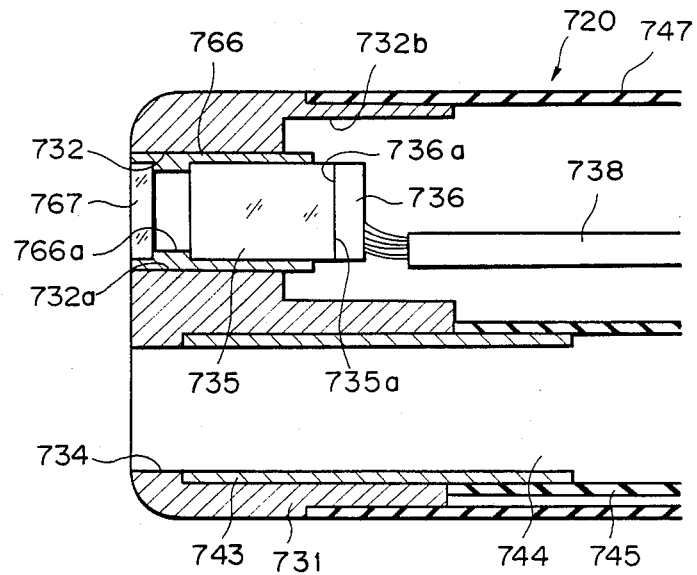
FIG. 59 is an enlarged vertical sectional view of a modified form of the distal end portion of the flexible electronic endoscope according to the twenty-eighth embodiment.
Figure 62:
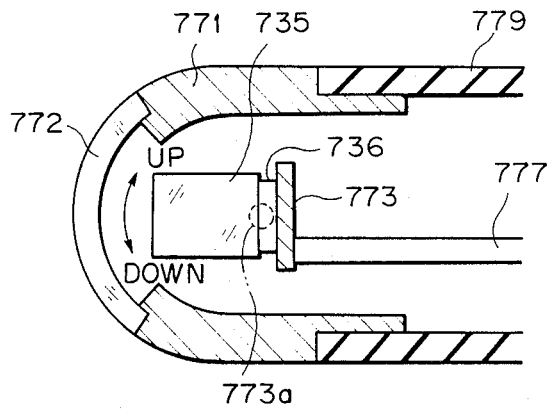
FIG. 62 is a sectional view taken along the line C—C' of FIG. 61.

The distal end portion 720 is constructed as illustrated in FIGS. 59 and 62.

The distal end portion 720 is provided with a columnar end body 713 made of a hard material such as a metal. As shown in FIG. 59, the end body 713 has an observation through-hole 732 which extends parallel to the longitudinal axis of the inserting section 712, illumination through-holes 733 (for example, two in number), and an instrument channel through-hole 734, as well as an air supply channel and a water supply channel (neither of which is shown).

Referring back to FIG. 56, the observation through-hole 732 has a small diameter portion 732a at its front end and a large diameter portion 732b at its rear end, and a self-convergence rod lens (such as one sold under the tradename of "SELFOC") 735 is fitted into the observation through-hole 732 as a focusing optical system. The self-convergence rod lens has an index of refraction which reaches its maximum on the optical axis and which gradually decreases in the radial direction, and an image is transferred by repetitive focusing at predetermined intervals in the self-convergence rod lens. In the twenty-eighth embodiment, the rear end of the rod lens 735 projects into the large diameter portion 732, and the rear end surface of the rod lens 735 serves as a focal surface 735a. A solid state imaging device 736 such as a CCD is bounded to the rear end surface of the rod lens 735 in such a manner that a light receiving surface 736a may abut against the focal surface 735a. The solid state imaging device 736 is connected to a signal cable 738, and the signal cable 738 is inserted into the inserting section 712 and the universal cord 714 and is connected to the connector 715.

Projection lenses 741 are fitted into the illumination through-holes 733, respectively, and a light guide fiber bundle (not shown) is connected to the rear end of each of the projection lenses 741. The light guide fiber bundles are inserted into the inserting section 712 and the universal cord 714 and are connected to the connector 715.

A channel pipe 743 is fitted into the instrument channel through-hole 734, and an instrument channel tube 745 is connected to the rear end of the channel pipe 743 which forms the instrument channel 744. The instrument channel tube 745 extends through the inserting section 712 and is connected to the insertion port 722.

Figure 57:
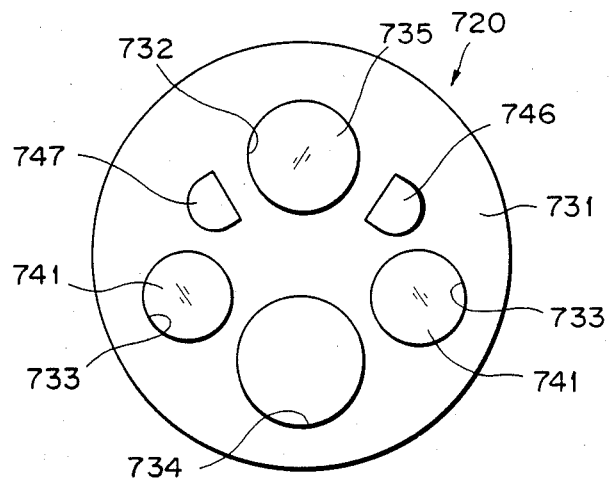
FIG. 57 is an end view taken from the left-hand side of FIG. 55.

As shown in FIG. 57, an air supply nozzle 746 and a water supply nozzle 747 which are opened toward the observation through-hole 732 are provided at the front ends of the air supply channel through-hole and the water supply channel through-hole, respectively. An air supply channel tube and a water supply channel tube (neither of which is shown) are connected to the air supply nozzle 746 and the water supply nozzle 747, respectively. These tubes extend through the inserting section 712 and the universal cord 714 and are connected to the connector 715.

A flexible tube 747, which forms the shell of the inserting section 712, is connected to the end body 713 at the rear end thereof.

If a frame sequential system is employed as a color imaging system, the light source device incorporated in the control apparatus 716 is provided with, for example, a light source lamp and a rotary color filter which is disposed ahead of the light source lamp and which has three color filters for each transmitting a different one of red (R), green (G) and blue (B). Illumination light emitted from the light source lamp is sequentially separated into color elements each having a different one of the wavelengths of red (R), green (G) and blue (B), converged by a condenser lens, and made incident upon the light entrance end of the light guide fiber bundle which axially extends in the electronic endoscope 711 connected to the control apparatus 716.

On the other hand, if a simultaneous system is employed as a color imaging system, the light source device of the control apparatus 716 is arranged so that white light emitted from a white light source may be made incident upon the light entrance end of the light guide fiber bundle. The illumination light is conducted to the end portion 720 through the aforesaid light guide fiber bundle, emitted from the light exit end of the end portion 720, and projected onto an object by the projection lenses 741.

An image of the object illuminated by the illumination light is focused onto a focal surface 735a of the rod lens 735 at the rear end thereof by the self-convergence rod lens 735 serving as a focusing optical system, and the thus-focused image is received by the light receiving surface 736a of the solid state imaging device 736 which abuts against the focal surface 735a. The solid state imaging device 736 is driven by a driving circuit incorporated in the control apparatus 716, and image signals read from the device 736 are supplied to a signal processing circuit incorporated in the control apparatus 716. Then, video signals, which are generated by the signal processing circuit, are supplied to the color monitor 717, and the object image is displayed on the color monitor 717.

If the aforesaid simultaneous system is used as a color imaging system, a color filter array constituted by a mosaic arrangement of three color filters for each transmitting a different one of colors such as R, G and B is disposed on the optical axis ahead of the light receiving surface 736a of the solid state imaging device 736.

As described above, the focusing optical system is constituted by the self-convergence rod lens 735, and the solid state imaging device 736 such as a CCD is bonded to the rear end surface of the rod lens 735 in such a manner that the light receiving surface 736a may abut against the focal surface 735a of the rod lens 735 at the rear end thereof.

Accordingly, the structure of the portion between the focusing optical system and the solid state imaging device 736 is simplified, and easy assembly is enabled. Furthermore, since the light receiving surface 736a of the solid state imaging device 736 abuts against the focal surface 735a of the rod lens 735, the focusing optical system and the solid state imaging device 736 can be readily positioned.

Figure 58:
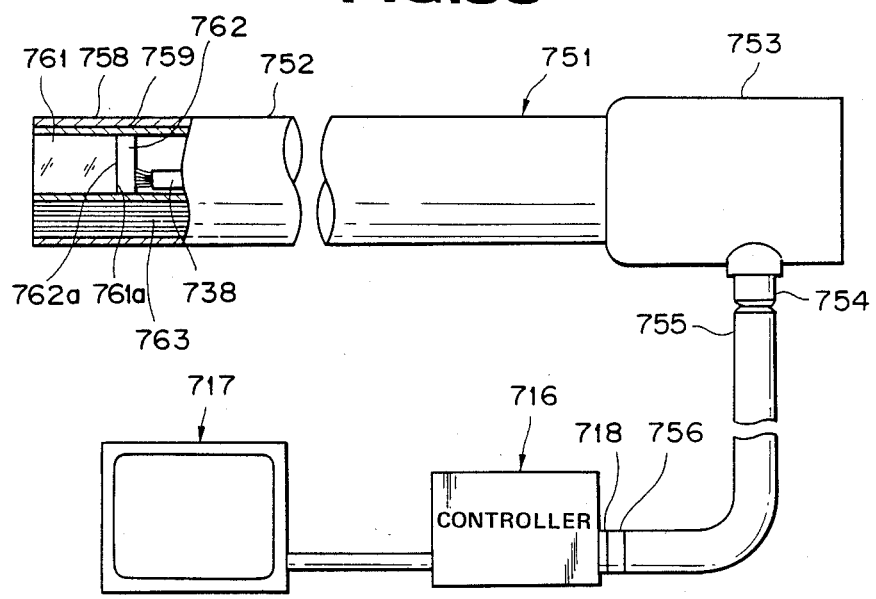
FIG. 58 is a diagrammatic, partially sectional view of a rigid electronic scope system to which the twenty-eighth embodiment is applied.

FIG. 58 shows an example of the twenty-eighth embodiment which is applied to a rigid electronic scope.

As shown in FIG. 58, a rigid electronic endoscope 751 is comprised of an elongated rigid inserting section 752 and a large diameter portion 753 connected to the rear end of the inserting section 752, and a connector 754 is attached to the operating section 753 on one side thereof, a light guide cable 755 being connected at one end thereof to the connector 754. In this example, the connector 754 also serves as a signal connector through which signals are transmitted to and received from a solid state imaging device. In addition to a light guide fiber bundle, a signal cable is inserted into the light guide cable 755. A connector 756 is attached to the other end of the light guide cable 755, and the connector 756 is connected to the connector receptacle 718 of the control apparatus 716.

An internal tube 759 is inserted into an external tube 758 which constitutes a portion of the inserting section 752, and a self-convergence rod lens 761 as a focusing optical system is attached to the internal tube 759 at the distal end thereof. A solid state imaging device 762 such as a CCD is bonded to the rear end of the rod lens 761 in such a manner that a light receiving surface 762a may abut against a focal surface 761a of the rod lens 761 at the rear end thereof. A signal cable 738 is connected to the solid state imaging device 762, and the signal cable 738 extends through the inserting section 752 and is connected to the connector 754.

A light guide fiber bundle 763 is inserted into the space between the internal tube 759 and the external tube 758, and the proximal end of the light guide fiber bundle 763 is connected to the connector 754.

In this embodiment as well, the structure of the portion between the focusing optical system and the solid state imaging device 762 is simplified, and easy assembly is enabled.

FIG. 59 is a vertical sectional view showing the end portion of a rigid electronic scope according to a modified form of the twenty-eighth embodiment.

In this modified form, a lens frame 766 is fitted into a small diameter portion 732a of an observation through-hole 732 of an end body 731. A cover glass 767 is fitted into the lens frame 766 at the front end thereof, and the self-convergence rod lens 735 as a focusing optical system is mounted behind the cover glass 767, with a stepped portion 766a having a predetermined axial length interposed therebetween. The solid state imaging device 736 such as a CCD is bonded to the rear end surface of the rod lens 735 in such a manner that a light receiving surface 736a may abut against a focal surface 735a of the rod lens 735 at the rear end thereof.

The modified form shown in FIG. 59 can be applied to a rigid electronic scope such as is shown in FIG. 58. In this case, the cover glass 767 and the lens frame 766 for holding the rod lens to which the solid state imaging device 736 is bonded may be mounted in the internal tube 759 at the distal end thereof.

Figure 60:
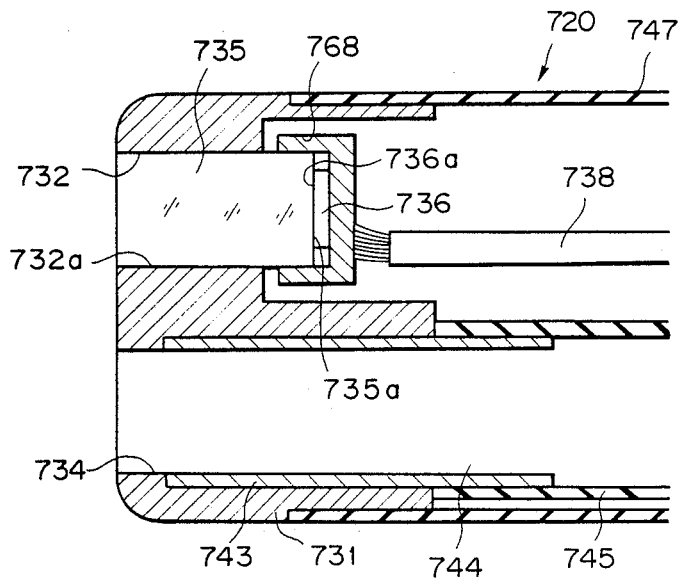
FIG. 60 is an enlarged vertical sectional view of another modified form of the distal end portion of the flexible electronic endoscope according to the twenty-eighth embodiment.

FIG. 60 is a vertical sectional view showing the end portion of a flexible electronic scope according to another modified form of the twenty-eighth embodiment which employs a self-convergence rod lens.

Figure 56:
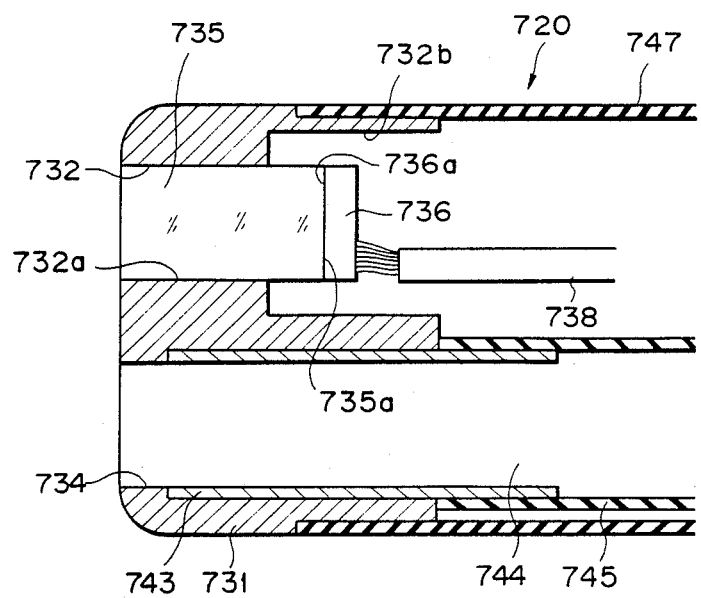
FIG. 56 is an enlarged vertical sectional view of the distal end portion of the flexible electronic endoscope shown in FIG. 55.

Similarly to the modified form shown in FIG. 56, the self-convergence rod lens 735 as a focusing optical system is attached to the small diameter portion 732a of the observation through-hole 732 of the end body 731. The solid state imaging device 736 is held by a device frame 768, and the device frame 768 is fixed to the rod lens 735 at the rear end thereof in such a manner that the focal surface 735a of the rod lens 735 at the rear end thereof abuts against the light receiving surface 736a.

It is to be noted that each of the above-described modified forms may be provided with a flexible inserting section.

Figure 61:
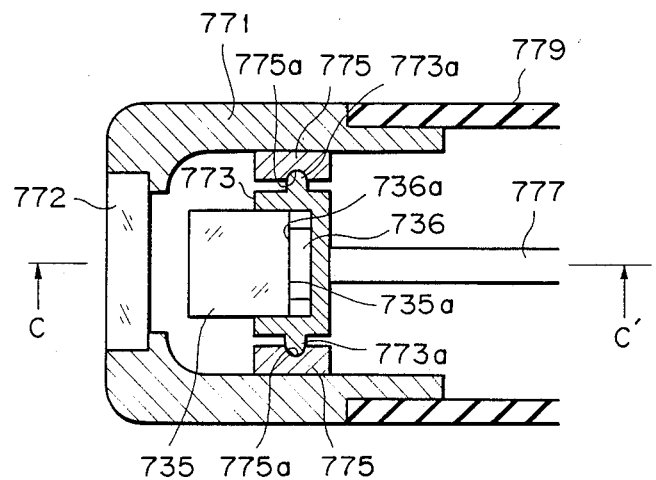
FIG. 61 is an enlarged vertical sectional view of still another modified form of the distal end portion of the flexible electronic endoscope according to the twenty-eighth embodiment.

In the flexible electronic scope shown in FIG. 61, a cover glass 772 having, for example, an outwardly curved surface as shown in FIG. 62 is fitted into an observation window (opening) formed in the front end of an end body 771. A tube 779 which constitutes the shell of the inserting section and which has, for example, a flexible body is connected to the rear end of the end body 771.

Similarly to the modified form shown in FIG. 60, the end body 771 accommodates the self-convergence rod lens 735 held by the device frame 773 and serving as a focusing optical system; and the solid state imaging device 736 having the light receiving surface 736a which abuts against the focal surface 735a of the rod lens 735 at the rear end thereof. As shown in FIG. 61, engagement pins 773a and 773b project from the device frame 773, for example, on the horizontally opposite sides thereof. On the other hand, support members 775 are fixed to the inner periphery of the end body 771 at locations which oppose the engagement pins 773a and 773b. Engagement grooves 775a are formed in the support members 775, and the engagement pins 773a are engaged with the engagement grooves 775a, respectively. As shown in FIG. 62, the solid state imaging device 773 are vertically pivotable about the engagement pins 773a.

A signal cable 777 having proper rigidity and serving as an operating wire penetrates the solid state imaging device 773 at a vertically biased location thereof (as viewed in FIG. 62), and is connected to the solid state imaging device 736. The signal cable 777 extends through an inserting section and is led out therefrom or connected to an operating knob which is disposed on the inserting section for changing the axis of view.

As shown in FIG. 62, when the signal cable 777 is moved to the front (to the left in FIG. 62), the solid state imaging device 773 is pivoted upwardly, and the solid state imaging device 736 and the rod lens 735 both of which are fixed to the device frame 773 are pivoted upwardly, whereby the visual field for observation is directed upwardly. On the other hand, when the signal cable 777 is moved to the rear (to the right in FIG. 62), the device frame 773 is pivoted downwardly and the solid state imaging device 736 and the rod lens 735 are pivoted downwardly, whereby the visual field for observation is directed downwardly.

Illumination windows are disposed, for example, at four corners, around the cover glass 772 which covers the observation window formed in the end body 771 at the front end thereof. The light guide fiber bundle is arranged by passing around the rod lens 735 and the solid state imaging device 736.

As described above, the structure of the portion between the focusing optical system and the solid state imaging device 736 is simplified, and easy assembly is enabled. The conversion of the direction of the visual field can be achieved by a simple construction.

It is to be noted that, although the solid state imaging device 773 may be pivoted in one direction, it may be arranged for pivotal movement in two or more directions. An operating wire operated to cause pivotal movement of the device frame 773 may be separated from the signal cable 777.

In this modified form, the inserting section may be of a flexible or rigid type.

It is to be noted that, the whole of the focusing optical system need not necessarily be constituted by the above-described self-convergence rod lens and, for example, the front side of the focusing optical system may be constituted by an objective lens and a self-convergence rod lens and a solid state imaging device may be disposed behind the objective lens.

While the above provides a full and complete disclosure of the invention, various modifications, alternative constructions and equivalents may be employed without departing from the true spirit and scope of the invention. Therefore, the above description and illustrations should not be construed as limiting the scope of the invention, which is defined solely by the appended claims.

What is claimed is:

1. A rigid endoscope comprising:
   an elongated rigid inserting section;
   an objective lens system provided in said inserting section at the distal end thereof for forming an optical image of an object;
   a relay optical system inserted into the interior of said inserting section and opposing at one end surface said objective optical system, said optical image being transferred through said relay optical system from said one end surface to the other end surface; and
   a disconnectable solid state imaging device disconnectably attached to said inserting section at a focus position on which said optical image transferred through said relay optical system is formed.

2. A rigid video endoscope according to claim 1, wherein said inserting section includes a light guide for transferring illumination light.

3. A rigid video endoscope comprising:
an elongated rigid inserting section;
a light guide inserted into said inserting section and having a light entrance end for receiving illumination light and a light exit end for allowing said illumination light to be passed therethrough;
an objective lens system provided in said inserting section at the distal end thereof for forming an optical image of an object;
a relay optical system for transferring said optical image formed by said objective optical system;
a solid state imaging device disposed at a focus position on which said optical image transferred through said relay optical system is formed; and
a visual field mask disposed within the relay optical system at one of focus positions in an optical axis extending from said objective optical system through said relay optical system to an imaging surface of said solid state imaging device.

4. A rigid video endoscope comprising:
an elongated rigid inserting section;
an objective lens system provided in said inserting section at the distal end thereof for forming an optical image of an object;
a relay optical system inserted into the interior of said inserting section and opposing said objective optical system at its one end, said optical image being transferred through said relay optical system from said one end surface to the other end surface;
a beam splitter disposed in face-to-face relationship with the light exit surface of said relay optical system for separating said optical image into image elements and outputting said image elements;
an eyepiece window disposed on the side of said beam splitter from which one of said separated image elements are output; and
a solid state imaging device disposed at a focus position upon which the other of said image elements separated by said beam splitter is focused.

5. A rigid video endoscope according to claim 2, 3 or 4, further including focus adjusting means for varying the optical distance between said light exit end of said relay optical system and said imaging surface of said solid state imaging device.

6. A rigid video endoscope according to claim 2, 3 or 4, wherein said relay optical system is comprised of a lens tube and a plurality of lenses arranged in series within said lens tube.

7. A rigid video endoscope according to claim 2, 3 or 4, wherein said relay optical system is constituted by gradient index lenses.

8. A rigid video endoscope according to claim 2, 3 or 4, wherein said objective optical system and said relay optical system are constituted by gradient index lenses, respectively.

9. A rigid video endoscope according to claim 2, 3 or 4, further including an infrared cutoff filter disposed ahead of said imaging surface of said solid state imaging device.

10. A rigid video endoscope according to claim 2, 3 or 4, wherein a color separating filter is disposed on said imaging surface ahead of said solid state imaging device.

11. A rigid video endoscope according to claim 2, 3 or 4, wherein said objective optical system has an optical axis parallel to the axial direction of said inserting section.

12. A rigid video endoscope according to claim 2, 3 or 4, wherein said objective optical system has an optical axis which is not parallel to but inclined with respect to the axial direction of said inserting section.

13. A rigid video endoscope according to claim 2, 3 or 4 having a watertight structure for preventing a liquid from entering the interior of said rigid video endoscope.

14. A rigid video endoscope according to claim 4, further including an imaging unit which accommodates said solid state imaging device, said imaging unit having detachable connecting means at a location opposing said beam splitter.

15. A rigid video endoscope according to claim 2 or 4, further including a visual field mask disposed at a focus position of said relay optical system.

16. A rigid video endoscope system, comprising:
a rigid endoscope section including:
an elongated rigid inserting section;
a light guide inserted into said inserting section and having a light entrance end for receiving illumination light and a light exit end for allowing said illumination light to be passed therethrough;
an objective lens system provided in said inserting section at the distal end thereof for forming an optical image of an object;
a relay optical system for transferring said optical image formed by said objective optical system; and
a solid state imaging device disposed at a focus position on which said optical image transferred through said relay optical system is formed;
an eyepiece unit including:
first connecting means for detachably attaching said eyepiece unit to said rigid endoscope section;
an eyepiece lens disposed in a face-to-face relationship with the light exit end of said relay optical system when said eyepiece unit is attached to said rigid endoscope section;
an eyepiece window disposed on the light exit side of said eyepiece lens; and
an imaging unit including:
second connecting means for detachably attaching said eyepiece unit to said rigid endoscope section; and
a solid state imaging device disposed at a focus position of said relay optical system when said eyepiece unit is attached to said rigid endoscope section by said second connecting means.

17. A rigid endoscope system, comprising:
a rigid endoscope including:
an elongated rigid inserting section,
a light guide inserted into said inserting section and having a light entrance end for receiving illumination light and a light exit end for allowing said illumination light to be passed therethrough,
an objective lens system provided in said inserting section at the distal end thereof for forming an optical image of an object,
a relay optical system for transferring said optical image formed by said objective optical system, and
a disconnectable solid state imaging device disconnectably connected to said inserting section at a focus position of said relay optical system;

a visual field mask disposed within the relay optical system;

illumination light supplying means for supplying illumination light to the light entrance end of said light guide;

signal processing means for effecting signal processing of output signals from said solid state imaging device; and display means for providing a visual display of video signals output from said signal processing means.

18. A rigid video endoscope system according to claim 16 or 17, wherein said relay optical system is comprised of a lens tube and a plurality of lenses arranged in series within said lens tube.

19. A rigid video endoscope system according to claim 16 or 17, wherein said relay optical system is constituted by gradient index lenses.

20. A rigid video endoscope system according to claim 16 or 17, further including an infrared cutoff filter disposed ahead of said imaging surface of said solid state imaging device.

21. A rigid video endoscope system according to claim 16 or 17, wherein said solid state imaging device constitutes color imaging means of a built-in color filter type which includes a color separating filter disposed on the imaging surface of said solid state imaging device.

22. A rigid video endoscope system according to claim 16 or 17, wherein said solid state imaging device constitutes color imaging means of a frame sequential type having no color filter in front of an imaging surface of said imaging device.

23. A rigid video endoscope system according to claim 16, wherein said imaging unit has a magnifying lens for forming an enlarged image.

24. A rigid video endoscope system according to claim 16, wherein said rigid endoscope section includes a housing which accommodates the light exit end of said relay optical system; and a transparent member for covering the portion of said housing which opposes said light exit end of said relay optical system.

25. A rigid video endoscope system according to claim 16, wherein said eyepiece unit further includes a transparent member for covering the end of said eyepiece unit that corresponds to the light entrance face of said eyepiece lens.

26. A rigid video endoscope system according to claim 16, wherein said imaging unit has a housing for accommodating said solid state imaging device, the portion of said housing which opposes said imaging surface of said imaging device being covered by a transparent member.

27. A rigid video endoscope system according to claim 16, wherein said rigid endoscope section has a watertight structure.

28. A rigid video endoscope system according to claim 16, wherein said eyepiece unit has a watertight structure.

29. A rigid video endoscope system according to claim 16, wherein said eyepiece unit has a watertight structure.

30. A rigid video endoscope system according to claim 17, wherein said rigid video endoscope has a watertight structure.

31. A rigid video endoscope system according to claim 17, wherein said illumination light supplying means is constituted by a lamp which radiates white light.

32. A rigid video endoscope system according to claim 17, wherein said illumination light supply means is constituted by frame-sequentially light outputting means for sequentially in time outputting light having at least three different wavelengths.

33. A rigid video endoscope system according to claim 32, wherein said frame sequential light outputting means includes a lamp for outputting white light, a rotary color filter constituted by three color filters for each transmitting light having a different wavelength and a rotary wheel which carries said three color filters, and a motor for causing rotation of said rotary color filter to sequentially locate each of said color filters on the optical axis of said lamp.

34. A rigid video endoscope system according to claim 21, wherein said signal processing means effects signal processings which correspond to said color imaging means of a built-in color filter type.

35. A rigid video endoscope system according to claim 21, wherein said signal processing means effects said color imaging means of a frame sequential type having no color filter.

* * * * *

UNITED STATES PATENT AND TRADEMARK OFFICE
CERTIFICATE OF CORRECTION

PATENT NO. :  4,905,082

DATED     :  February 27, 1990

INVENTOR(S) :  NISHIGAKI et al

It is certified that error appears in the above-identified patent and that said Letters Patent is hereby corrected as shown below:

On the cover page, Item [75], "Hiroyuki Kusnoki" should read

--Hiroyuki Kusunoki--.

Signed and Sealed this

Tenth Day of September, 1991

Attest:

HARRY F. MANBECK, JR.

*Attesting Officer*  *Commissioner of Patents and Trademarks*